(12) United States Patent
Li

(10) Patent No.: US 9,976,717 B2
(45) Date of Patent: *May 22, 2018

(54) ELECTRONIC FLAMELESS CANDLE

(71) Applicant: Xiaofeng Li, Shenzhen (CN)

(72) Inventor: Xiaofeng Li, Shenzhen (CN)

(*) Notice: Subject to any disclaimer, the term of this patent is extended or adjusted under 35 U.S.C. 154(b) by 0 days. days.

This patent is subject to a terminal disclaimer.

(21) Appl. No.: 15/634,912

(22) Filed: Jun. 27, 2017

(65) Prior Publication Data

US 2017/0292666 A1   Oct. 12, 2017

Related U.S. Application Data

(60) Continuation of application No. 15/489,589, filed on Apr. 17, 2017, now Pat. No. 9,752,740, which is a
(Continued)

(51) Int. Cl.
*F21V 23/04* (2006.01)
*F21S 10/04* (2006.01)
(Continued)

(52) U.S. Cl.
CPC ............... *F21S 10/04* (2013.01); *A61L 9/127* (2013.01); *F21S 6/001* (2013.01); *F21S 9/02* (2013.01); *F21V 23/04* (2013.01); *H05B 33/0845* (2013.01); *H05B 37/0272* (2013.01); *H05B 37/0281* (2013.01); *A61L 2209/12* (2013.01);
(Continued)

(58) Field of Classification Search
None
See application file for complete search history.

(56) References Cited

U.S. PATENT DOCUMENTS 5,152,602 A   10/1992   Boschetto
9,644,807 B1   5/2017   Harris
(Continued)

FOREIGN PATENT DOCUMENTS

CN          102748589 A      10/2012
WO     WO 2010/009575 A1    1/2010

OTHER PUBLICATIONS

Extended European Search Report in European Application No. 14764844.8, dated Jul. 28, 2016.
(Continued)

*Primary Examiner* — Thomas M Sember
(74) *Attorney, Agent, or Firm* — Perkins Coie LLP

(57) ABSTRACT

An electronic flameless candle including a body having a top surface, a bottom surface, a sidewall between the top surface and the bottom surface, and a cavity defined by the top surface, the bottom surface and the sidewall, the body configured in shape and size to simulate a true flame candle. The candle may also include a light source operably connected to the body, the light source electrically operated to illuminate in a way that simulates a natural flicker of a real candle flame. The candle may also include a scent component, operably connected to the body, the scent component configured to emit a scent when heated and/or a sensor component, operably connected to the body, the sensor component configured to sense an environmental condition and affect a mode of the light source upon the sensing of the environmental condition.

19 Claims, 22 Drawing Sheets

Related U.S. Application Data continuation of application No. 15/187,618, filed on Jun. 20, 2016, now Pat. No. 9,625,112, which is a division of application No. 14/297,862, filed on Jun. 6, 2014, now Pat. No. 9,371,972, which is a continuation-in-part of application No. 14/213,287, filed on Mar. 14, 2014, now Pat. No. 9,360,181.

(60) Provisional application No. 61/798,527, filed on Mar. 15, 2013, provisional application No. 61/798,348, filed on Mar. 15, 2013, provisional application No. 61/798,053, filed on Mar. 15, 2013.

(51) Int. Cl.
| | |
|---|---|
| *F21S 9/02* | (2006.01) |
| *F21S 6/00* | (2006.01) |
| *H05B 37/02* | (2006.01) |
| *H05B 33/08* | (2006.01) |
| *A61L 9/12* | (2006.01) |
| *F21Y 115/10* | (2016.01) |

(52) U.S. Cl.
CPC ...... *A61L 2209/133* (2013.01); *F21Y 2115/10* (2016.08)

(56) References Cited

U.S. PATENT DOCUMENTS

| | | |
|---|---|---|
| 2003/0161145 A1 | 8/2003 | Liu |
| 2006/0120080 A1 | 6/2006 | Sipinski et al. |
| 2007/0002560 A1 | 1/2007 | Gutstein |
| 2007/0127249 A1 | 6/2007 | Medley et al. |
| 2007/0159422 A1 | 7/2007 | Blandino et al. |
| 2008/0074875 A1* | 3/2008 | Jensen ............. F21S 6/001 362/240 |
| 2008/0129226 A1 | 6/2008 | Dewitt |
| 2008/0151563 A1 | 6/2008 | Chen |
| 2009/0059596 A1 | 3/2009 | Lederer |
| 2010/0124050 A1 | 5/2010 | Hau |
| 2010/0134022 A1* | 6/2010 | Gutstein ............ F21S 6/001 315/152 |
| 2011/0317403 A1 | 12/2011 | Founier et al. |
| 2012/0093491 A1 | 4/2012 | Browder et al. |
| 2014/0140534 A1 | 5/2014 | Gutstein |

OTHER PUBLICATIONS

International Search Report and Written Opinion in International Application No. PCT/CN2014/073557, dated Jul. 2, 2014.

* cited by examiner

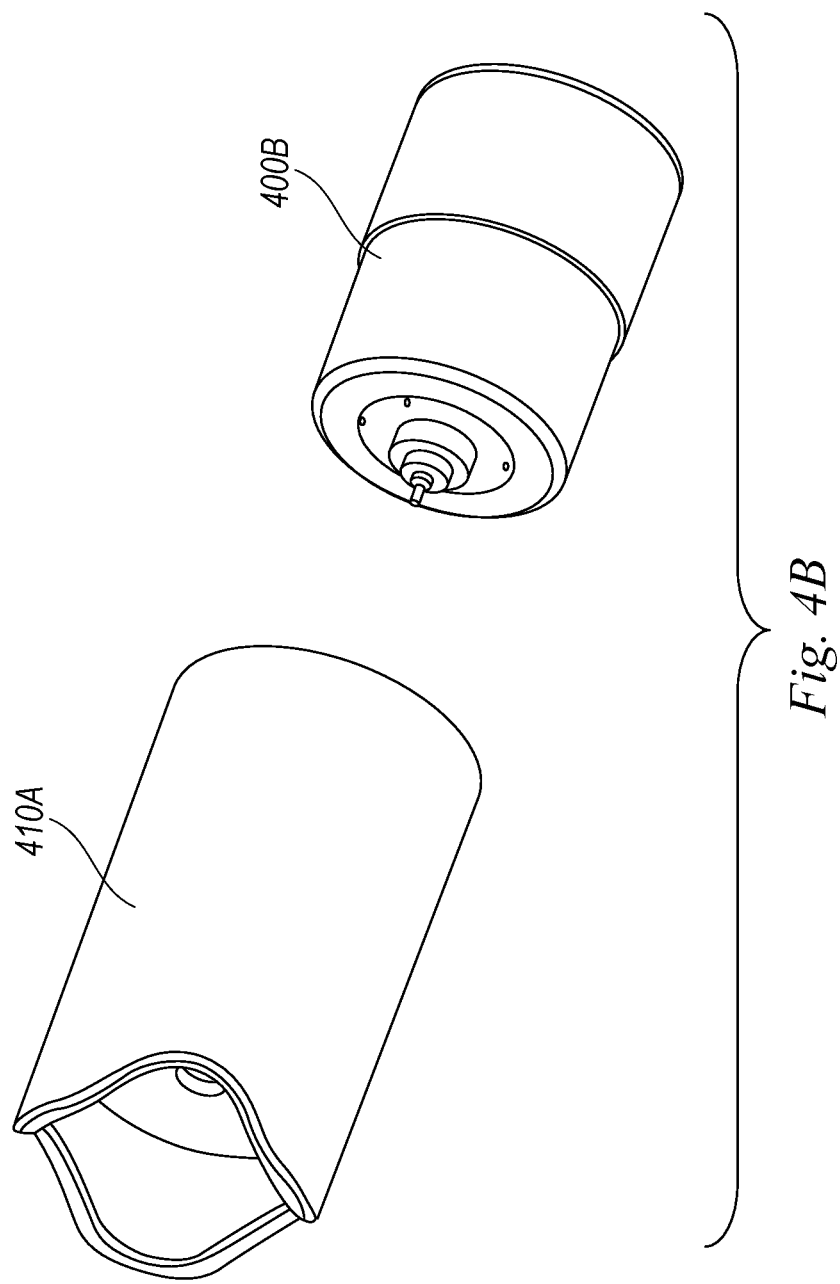

ELECTRONIC FLAMELESS CANDLE

CROSS-REFERENCE TO RELATED APPLICATIONS

This application is a continuation of U.S. patent application Ser. No. 15/489,589, filed Apr. 17, 2017, which is a continuation of U.S. application Ser. No. 15/187,618 filed Jun. 20, 2016, now U.S. Pat. No. 9,625,112, which is a division of U.S. patent application Ser. No. 14/297,862 filed Jun. 6, 2014, now U.S. Pat. No. 9,371,972, which is a continuation-in-part of U.S. patent application Ser. No. 14/213,287, filed on Mar. 14, 2014, now U.S. Pat. No. 9,360,1 81, entitled "Electronic Flameless Candle," and claims the benefit of U.S. provisional patent applications: Ser. No. 61/798,527, filed on Mar. 15, 2013, entitled "Flameless Candle;" Ser. No. 61/798,348, filed on Mar. 15, 2013, entitled "Scented Flameless Candle;" Ser. No. 61/798,053, filed on Mar. 15, 2013, entitled "Flameless Candle with Motion Sensor;" the disclosures of which are hereby incorporated by reference herein in their entirety.

FIELD OF THE INVENTION

The present disclosure relates to novel and advantageous flameless candles. Particularly, the present disclosure relates to novel and advantageous flameless candles simulating a realistic flame-like flicker, are capable of emitting a scent, and/or allow users to more easily control the candles' operations.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Traditional true flame candles, when lit, provide a pleasant ambience in many homes and businesses. Traditional candles may also be scented, adding a pleasant aroma. While the wax typically has a scent, even when the candle is not lit, this scent may be amplified when the candle is lit. Traditional candles however, provide a variety of hazards including risk of fire, damage to surfaces caused by hot wax, and the possible emission of soot. Flameless candles have become increasingly popular alternatives to traditional candles. With no open flame or hot melted wax, flameless candles provide a longer-lasting, safe, and clean alternative. There are flameless candles available that use incandescent lamps or light-emitting diodes (LEDs) as a light Source. However, such flameless candles are easily distinguishable from their traditional candle counterparts. One problem is that flameless candles generally cannot suitably simulate the natural flicker of an actual flame as viewed by the naked eye. Another problem is flameless candles have not been able to provide a scented feature that simulates the desired scented feature of a traditional candle, particularly when lit. In addition, flameless candles typically have one or more switches on the base of the candle to turn the candle on, off, or into a flicker mode. This requires the user to awkwardly or inelegantly take the candle off its resting place.

Thus, there is a need in the art for a flameless candle that is aesthetically similar to a traditional candle. More particularly, there is a need for a flameless candle that emits a more natural, flame-like flicker of light, is capable of emitting a scent, and allows the user to relatively easily control the candle's operations.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, relates to an electronic flameless candle. The candle may include a body having a top surface, a bottom surface, a sidewall between the top surface and the bottom surface, and a cavity defined by the top surface, the bottom surface and the sidewall, the body configured in shape and size to simulate a true flame candle. The candle may also include a light source operably connected to the body and positioned to be generally flush with an exterior surface of the body. The light source may be electrically operated to illuminate in a way that simulates a natural flicker of a real candle flame.

The present disclosure, in another embodiment, relates to an electronic flameless candle. The candle may include a control switch located on an exterior surface of a body of the electronic flameless candle, the control switch comprising a wick component configured in shape and size to simulate a true flame candle's wick.

The present disclosure, in another embodiment, relates to an electronic flameless candle. The candle may include a body comprising a top surface, a bottom surface, a sidewall between the top surface and the bottom surface, the body configured in shape and size to simulate a true flame candle. The candle may also include a cavity positioned within the body, the cavity defined by a top cavity surface, a bottom cavity surface, and a cavity sidewall surface between the top cavity surface and the bottom cavity surface, wherein the cavity surfaces are at least partially transparent. The candle may, in addition, include a light source operably configured in the body.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 4B is an exploded perspective view of a flameless pillar candle, according to an embodiment of the present disclosure.

DETAILED DESCRIPTION

The present disclosure relates to novel and advantageous flameless candles. Particularly, the present disclosure relates to novel and advantageous flameless candles simulating a realistic flame-like flicker, are capable of emitting a scent, and/or allow users to more easily control the candles' operations.

The present disclosure relates, in some embodiments, to a flameless candle that uses, in at least one embodiment, a LED light source to provide a natural, flame-like flicker of light. The flameless candle may include a body having a top surface, a bottom surface upon which the body rests, and a sidewall between the bottom surface and the top surface. One or more control switches may be located on the top surface, the bottom surface, or on the sidewall. Each of these control switches may provide a variety of functions or modes when activated separately or together, including, but not limited to, turning the light source on or off, operating the light source in static or random flicker mode, changing the color of the light, dimming or brightening of the light source, or activating a timer to change a function, such as turning the light off. The natural flicker may be created by a circuit board which provides a signal to the light. The signal may be comprised of random frequencies and amplitudes of current. The circuit board may also control pulse-width modulation and the frequency and duty ratio of the signal received by the light. The signal transmitted randomly to one or more of the diodes of the LED may cause the LED to produce a natural "flicker" of light to the human eye. In various embodiments, the flameless candle may alternatively or additionally include a scent diffusing component to diffuse a pleasant aroma into the surrounding area and/or a sensing component to sense one or more environmental conditions, including but not limited to, motion, light, or sound and control operation of the candle based on the sensed environmental condition.

A Flameless Candle

Figure 1A:
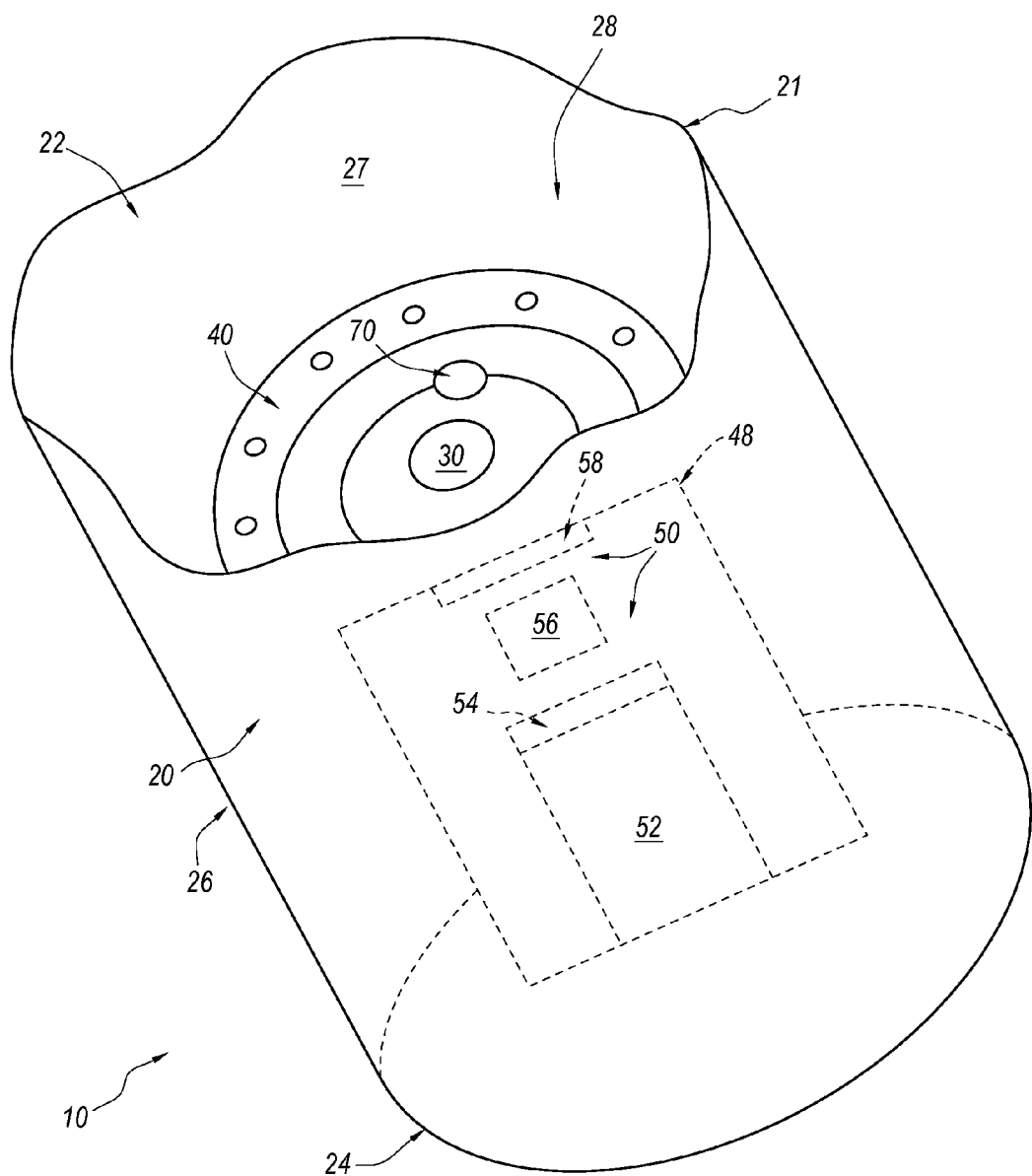
FIG. 1A is a perspective view of a flameless pillar candle, according to an embodiment of the present disclosure.

The flameless candles described herein provide a substantially more realistic flame-like light from a light source. In this regard, a flameless candle of the present disclosure may be comprised of one or more components that may function to mimic a natural flame's flicker. Referring to FIG. 1A, a flameless candle 10 may be comprised of a body 20, a control switch 30, and an electrical assembly 50. In various embodiments, the flameless candle 10 may also include a scent component 40, and a sensor component 70.

Structure

The Candle Body

Generally, as illustrated in the flameless pillar candle of FIG. 1A, the body 20 of a flameless candle 10 may be comprised of a top surface 22, a bottom surface 24 upon which the candle rests, and a sidewall 26 between the top surface 22 and the bottom surface 24. The body 20 may have desirable translucent, luminescent, and aesthetic properties to mimic the look and feel of a traditional candle. The body 20 may be made from one or more materials, including but not limited to, wax, paraffin, glass, polymeric materials, or any combination thereof.

Figure 1B:
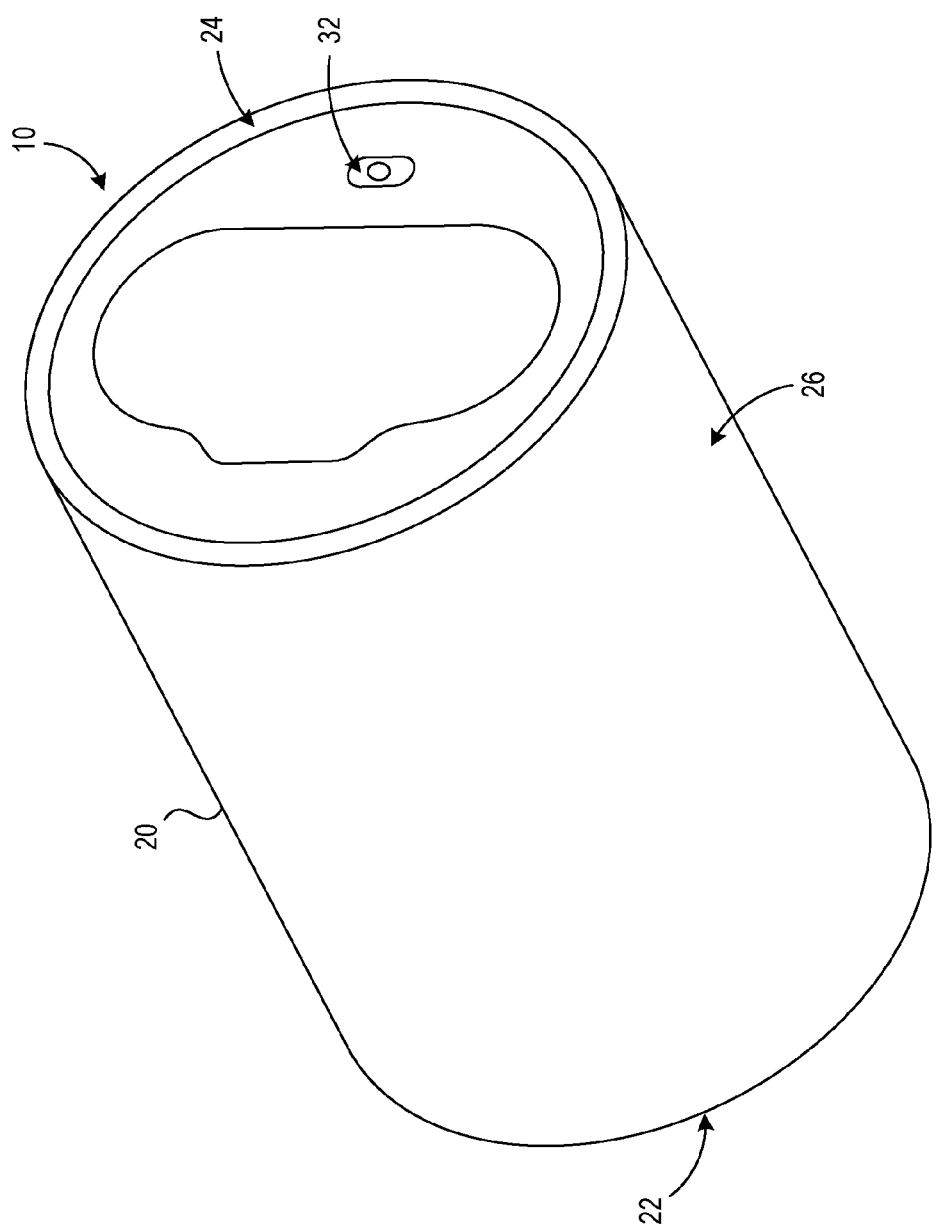
FIG. 1B is a bottom perspective view of a flameless pillar candle, according to an embodiment of the present disclosure.

The top surface 22 may generally refer to the top portion of the candle. The top surface 22 may include one or more structural components, in various embodiments. In one embodiment, the top surface 22 may include an indented central portion 28, a lip 21, an interior wall 27 between the lip 21 and the indented central portion 28. The indented central portion 28 may resemble the top surface of a used or partially melted traditional candle, where the wax may have been reduced by melting from the heat of the open flame in order to continue feeding the flame. In other embodiments, the central portion may not be indented. The sidewall 26 and interior wall 27 may cooperate to create a lip 21 on the top surface 22. As seen in the embodiment of FIG. 1A, the sidewall 26 and lip 21 may cooperate to have a varied height thereby resembling the visual appearance of a used traditional candle where the wax has been reduced. The sidewall 26 may have a constant height, in other embodiments. The top surface 22 and bottom surface 24 may be circular and the sidewall 26 may extend circumferentially around the longitudinal axis, resulting in a cylindrical body 20. However, other shapes or configurations are possible and within the scope of the invention including, but not limited to, a cube, a cuboid, a cone, a pyramid, or a sphere. The bottom surface 24 may generally be flat, resulting in a stable condition of the candle when placed on a table, shelf, or other suitable flat surface. The top surface 22, bottom surface 24, and sidewall 26 cooperate to form a cavity 48, schematically illustrated in FIG. 1A. As seen in FIG. 1B, the bottom surface 24 may also include a cover 34, that may allow easy access to the cavity 48.

Figure 1C:
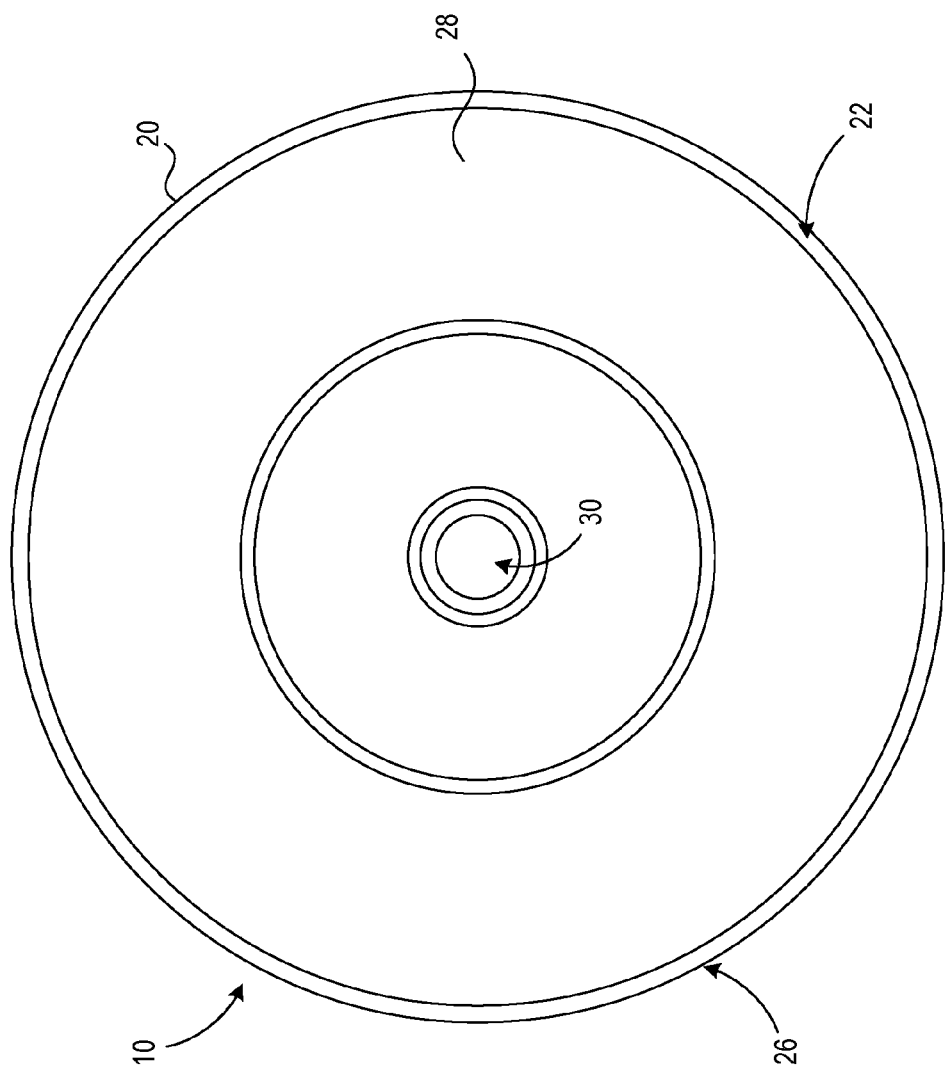
FIG. 1C shows a top view of a flameless candle, according to an embodiment of the present disclosure.
Figure 1D:
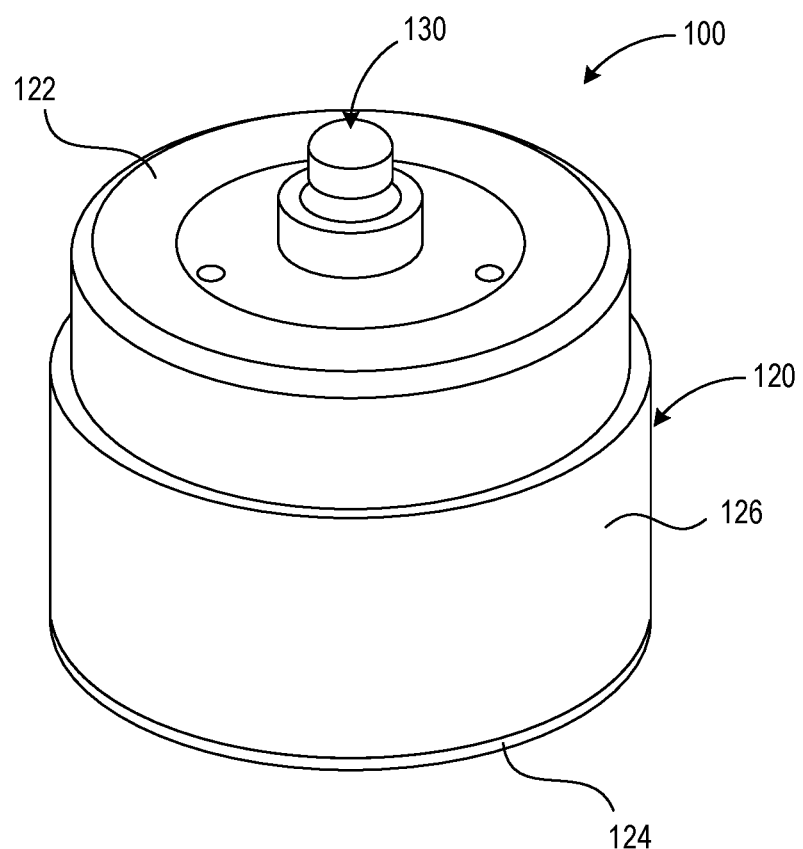
FIG. 1D is a perspective view of a flameless votive candle, according to an embodiment of the present disclosure.

Referring to FIG. 1D, the present disclosure may also be embodied in a votive flameless candle 100. The candle 100 may comprise a body 120. The body comprising a top side 122, a bottom side 124, and a sidewall 126 between the top surface 122 and bottom surface 124. Such a flameless candle 100 may generally be sized and shaped to simulate a traditional true flame votive candle, in some embodiments.

The Control Switch

Figure 3:
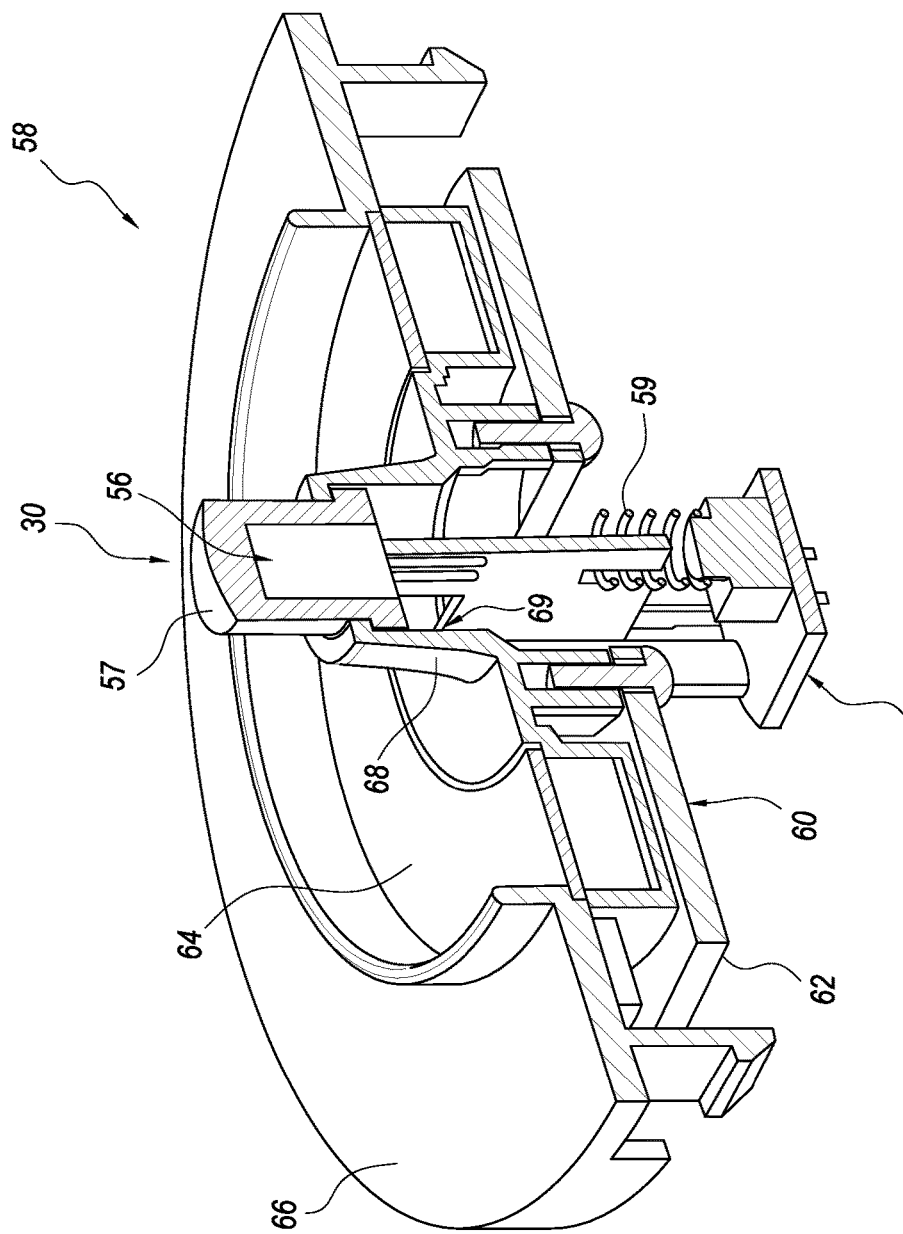
FIG. 3 is a cross-section of a control switch assembly, according to an embodiment of the present disclosure.

As illustrated in FIGS. 1A and 1C, disposed in the center of the base of the central portion 28 of top surface 22 may be an upper control switch 30. The upper control switch 30 may be a push button, toggle, slide, rotary selector switch, or any other suitable control. In at least one embodiment, the control switch 30 may activate or control all functions or modes of the candle, and in some cases, there may be no need for any additional control switches. In alternative or additional embodiments, the bottom surface 24 may include a lower control switch 32, as seen in FIG. 1B. An upper control switch 130 may also be seen in the embodiment in FIG. 1D. By activating the control switches 30 or 130 and/or 32 separately or in conjunction, one or more functions or modes may be activated, such as the light source 56 may begin to flicker. In at least one embodiment, the control switch 30 may house the light source 56, as seen in FIG. 3.

The Electrical Assembly

The cavity 48 may contain the electrical assembly 50, schematically illustrated in FIG. 1A. The electrical assembly may comprise one or more components, including, but not limited to, a control switch assembly 58 (shown in greater detail in FIG. 3), a power source 52, at least one circuit board 54, and a light source 56. The upper control switch 30 may be in communication with the light source 56 of the flameless candle 10. Or, as stated above, the control switch 30 may house the light source.

Control Switch Assembly

Figure 2:
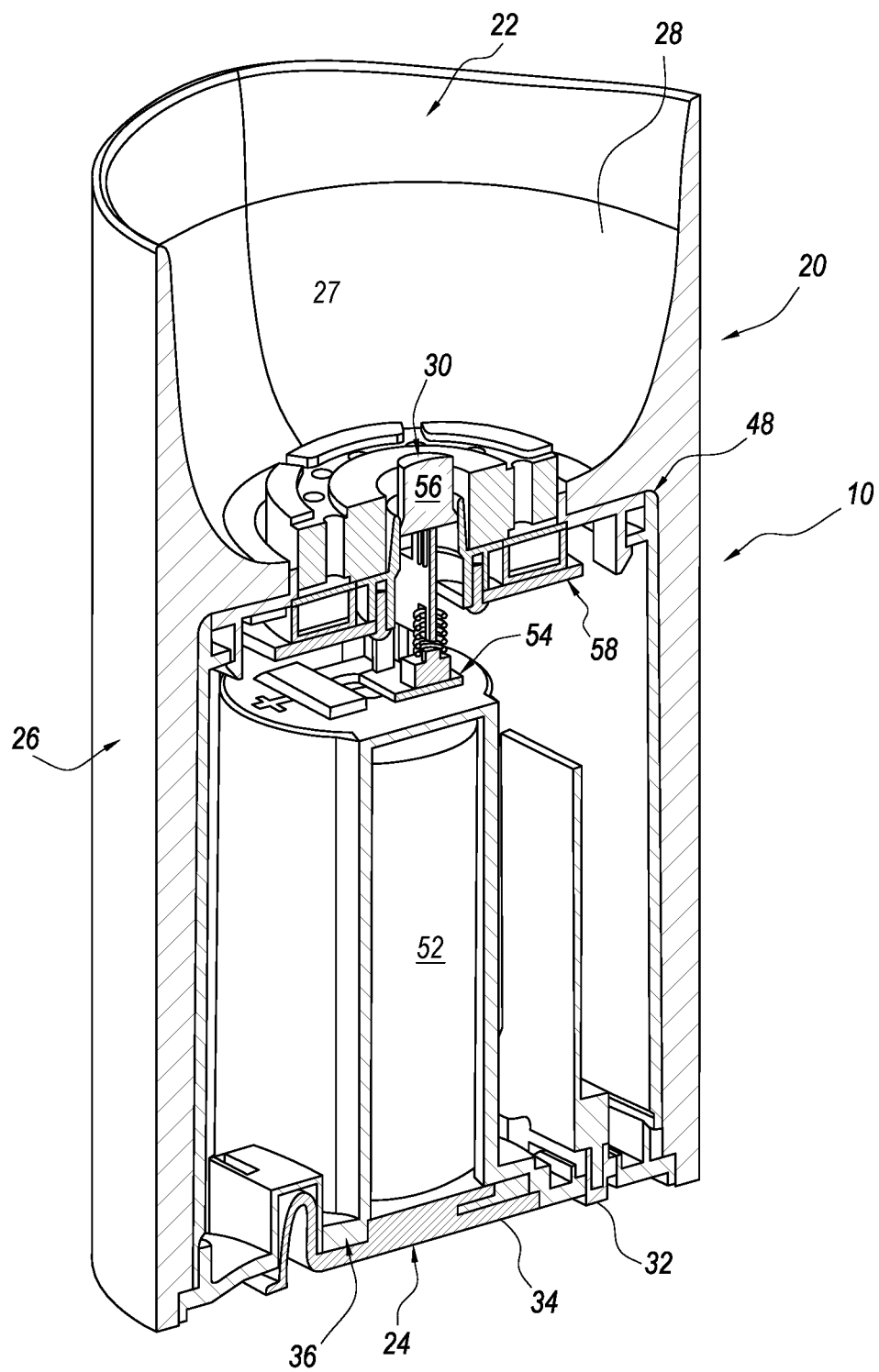
FIG. 2 is a cross-section of a flameless pillar candle, according to an embodiment of the present disclosure.

Referring to FIG. 2, the control switch assembly 58 may retain the control switch 30. The control switch assembly 58 may be comprised of one or more components. In one embodiment as seen in FIG. 3, the control switch assembly 58 components may include, but are not limited to, a push button control switch 30, a spring 59, and a retaining assembly 60. The spring 59 may be disposed between the light source 56 and the circuit board 54. In other embodiments, the light source may be positioned below the spring and the circuit board. The light source 56 may be brought into electrical and mechanical communication with the circuit board 54. For example, a push button control switch 30 may be pressed down so that it is in an "on" position resulting in the spring 59 compressing. The light source 56 may become electrically engaged with the circuit board 54. When the push button for the control switch is pressed down again, the spring 59 may release and the push button returns to an "off" position. In at least one such embodiment, when the spring 59 is released, the light source 56 is electrically disengaged from the circuit board 54. In other embodiments, for example those not using a push button, a spring may not be present.

The control switch assembly 58 may further comprise a retaining assembly 60. The retaining assembly 60 may have a circumferential outer conical portion 68 that mates with a circular opening within the top surface of the candle body. In at least one embodiment, the retaining assembly 60 may have a central lumen 69 through which the control switch 30 may be able to slide. In at least one embodiment, when installed within the top surface, the retaining assembly 60 is flush with the surrounding surface of the indented central portion 28 of the body 20. The retaining assembly 60 may comprise several components that are assembled to hold the control switch assembly 58 within the candle body. The components may, in some embodiments, comprise a plurality of concentric mating rings, each with a different inner and out diameter. In the embodiment of FIG. 3, there may be an inferior ring 62, a superior inner ring 64, and a superior outer ring 66. In various embodiments, the circumferential outer conical portion 68 may be comprised within the superior inner ring 64. While the retaining assembly 60 described and shown herein comprises a plurality of concentric mating rings, other shapes or configurations are possible and are within the scope of the invention. Such other shapes or configurations include but are not limited to cubes, rectangular solids, cones, pyramids, spheroids, and irregular shapes. In some embodiments, the retaining assembly components are integrally formed.

In some embodiments, the retaining assembly is made from a wax, paraffin, glass, polymeric materials, or combinations thereof. In some embodiments, the configuration of the retaining assembly 60 and the selected material may have desirable translucent, luminescent and aesthetic properties to mimic the look and feel of a traditional candle.

Power Source

Referring back to FIG. 2, the power source may provide power to the electrical assembly, resulting in the light source being illuminated. The power source 52 may be disposed within a power source compartment 36. As shown in the embodiment of FIG. 2, the power source 52 may comprise one or more batteries. The power source 52 may be adjacent to the cover 34 and centrally located, allowing an ease of access to change the battery.

In other embodiments, the power compartment may be located proximal to the sidewall 26, superior to the rest of the electrical assembly, or exterior to the flameless candle 10. The power compartment may be located in any suitable location. The power source may be one or more standard alkaline batteries, one or more rechargeable batteries, a USB charged power source, a power cord, a power source charged by induction charging, any other suitable source, or any combination thereof.

Light Source

The light source may illuminate the flameless candle. The light source may be a

LED that comprises one or more diodes, in various embodiments. The light source may be an incandescent lamp, in other embodiments. The light source may be a gas discharge lamp, in yet another embodiment. It should be understood that any suitable light source may be used. The light source may preferably be located on a midline of the body 20 of the candle in order to mimic traditional candles, as seen in FIG. 2. In other embodiments, the light source may be located more proximal to the sidewall. In at least one embodiment, the light source may be located superior to the transverse plane, or in the top half of the candle. However, a light source located at any point within the body of the candle is within the scope of the present disclosure.

Referring to FIG. 3, the light source 56 may be built into a customized housing 57, in some embodiments. The customized housing 57, in one embodiment, has a concave top surface, but in other embodiments can be convex or may be a flat top surface. The customized housing 57 may also have a concave bottom surface, convex bottom surface, or flat surface. In some embodiments, the customized housing 57 may be made of a clear, translucent or opaque material. In at least one embodiment, the customized housing may be coated with a plurality of specks of an orange or yellow coating arranged in a specific pattern to make the light appear more natural. In at least one embodiment, as shown in FIG. 3, the light source 56 and the customized housing 57 may form a push button of the control switch 30.

Turning now to FIGS. 4A-4G, other embodiments of an electronic flameless candle are shown. Generally, as illustrated in the flameless pillar candles of FIG. 4A and 4F, the body 420 of a flameless candle 400 may be comprised of a top surface 422, a bottom surface 424 upon which the candle rests, and a sidewall 426 between the top surface 422 and the bottom surface 424.

The body 420 may have desirable translucent, luminescent, and aesthetic properties to mimic the look and feel of a traditional candle. The body 420 may be made from one or more materials, including but not limited to, wax, paraffin, glass, polymeric materials, or any combination thereof.

Figure 4A:
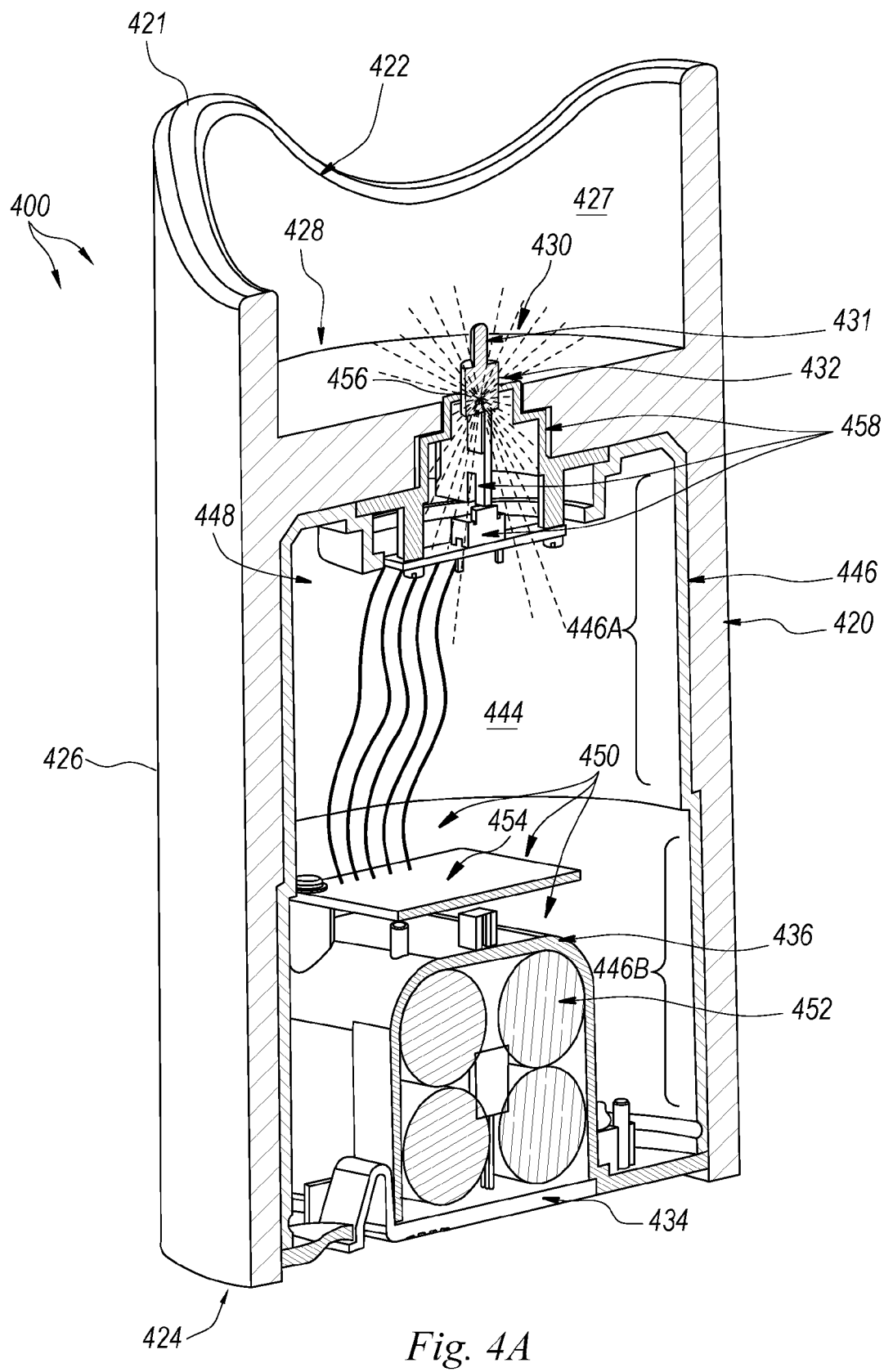
FIG. 4A is a perspective view of a flameless pillar candle, according to an embodiment of the present disclosure.
Figure 4C:
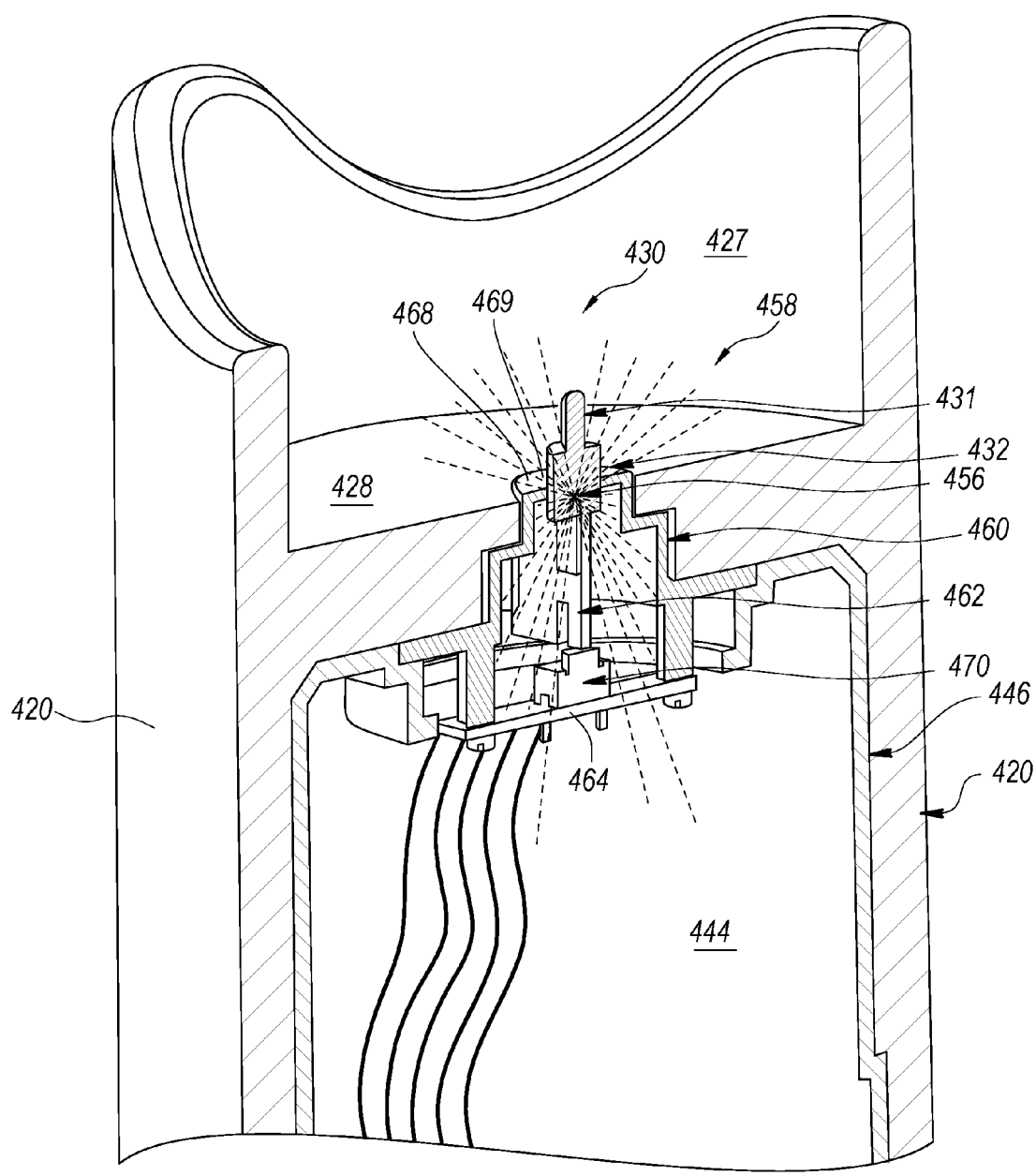
FIG. 4C is a perspective view of a retaining assembly, according to an embodiment of the present disclosure.
Figure 4D:
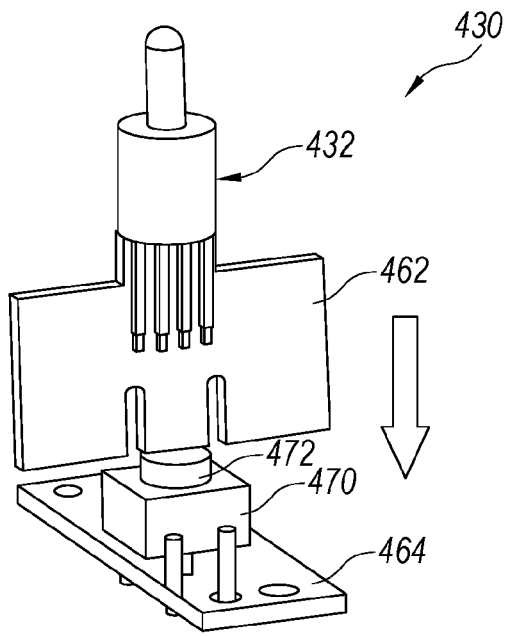
FIG. 4D is a perspective view of a control switch interacting with an internal push button, according to an embodiment of the present disclosure.
Figure 4E:
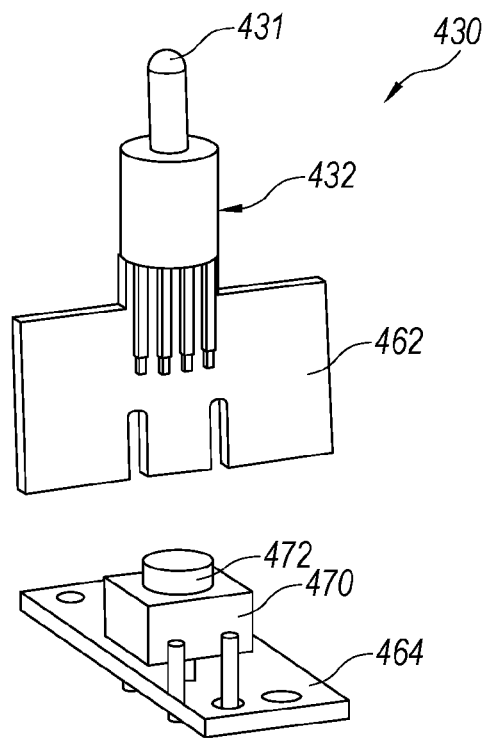
FIG. 4E is a perspective view of a control switch interacting with an internal push button, according to an embodiment of the present disclosure.
Figure 4F:
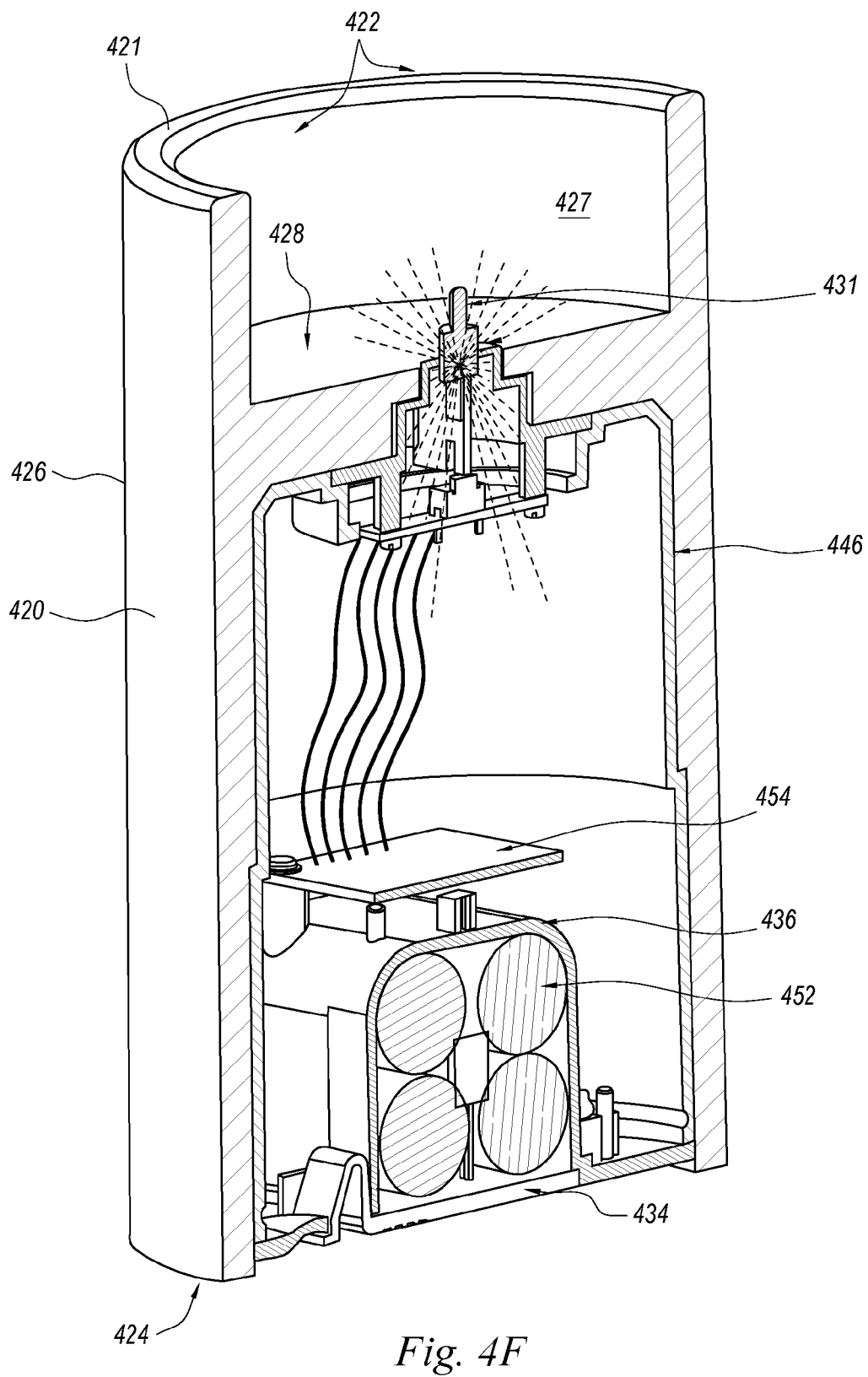
FIG. 4F is a perspective view of a flameless pillar candle, according to an embodiment of the present disclosure.
Figure 4G:
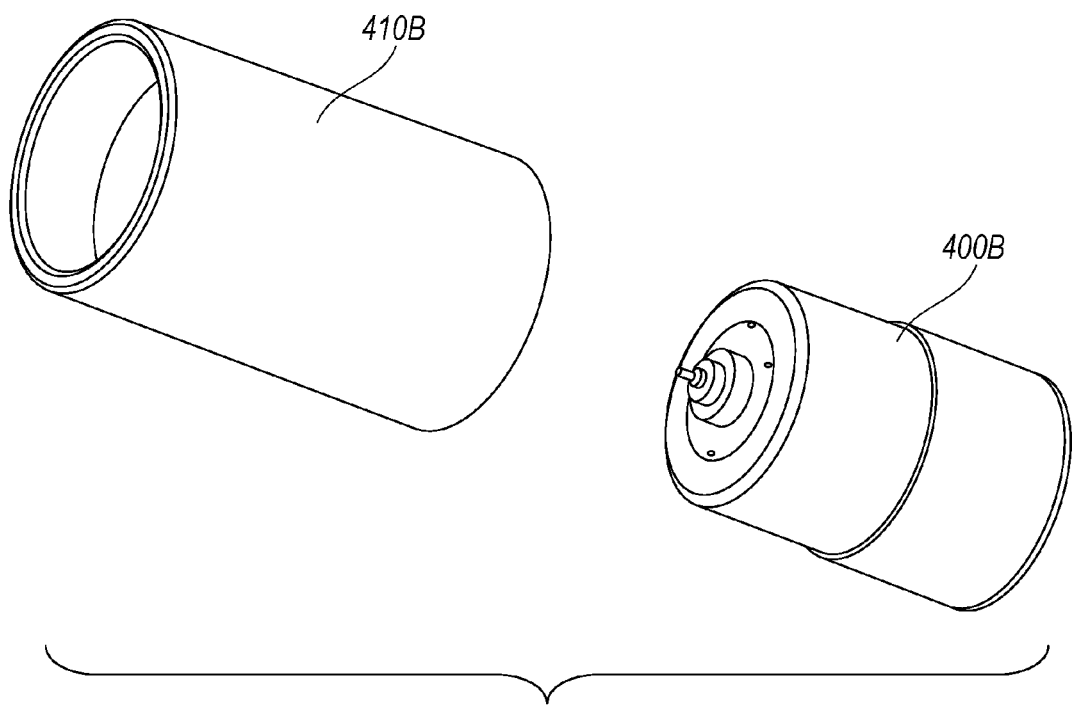
FIG. 4G is an exploded perspective view of a flameless pillar candle, according to an embodiment of the present disclosure.

Referring to FIGS. 4B and 4G, the flameless candle 400 may include an outer shell 410A, 410B and an inner core 400B. The outer shell 410A, 410B may be removed from the inner core 400B, in some embodiments. The inner core 400B may, in some embodiments, be used as a flameless candle without the outer shell 410A, 410B. In one embodiment, the inner core 400B may resemble a gel or oil candle. The inner core 400B may or may not resemble the appearance of a traditional candle type. It should be appreciated, in one embodiment, that a user may be able to select between multiple candle types (e.g., the outer shell and inner core in combination or just the inner core). The outer shell 410A, 410B may be replaced onto the inner core 400B. In various embodiments, the outer shell 410A, 410B may be mechanically connected to the inner core 400B, such that the sleeve may resist accidental removal. For example, the outer shell 410A, 410B may mechanically connect to the inner core 400B using a bayonet connection, a snap fit, a magnetic fit, a friction fit, or any other suitable method of connection. The outer shell 410A, 410B may additionally or alternatively be substantially permanently connected to the inner core 400B.

In addition, the outer shell 410A, 410B may additionally be exchanged, after removal, thereby allowing a user to vary between one or more aesthetic candle outer shell options. In one example only, a white outer shell 410A, 410B may be removed and a green sleeve may alternatively be mechanically connected to the inner core 400B, thus changing the pillar candle from white to green. It should be appreciated that any number of varying sleeves may be used to vary the color, transparency, texture, shape, height, scent (discussed more below), any other feature, or any combination thereof.

The top surface 422 may generally refer to the top portion of the candle. The top surface 422 may include one or more structural components, in various embodiments. In one embodiment, the top surface 422 may include an indented central portion 428, a lip 421, an interior wall 427 between the lip 421 and the indented central portion 428. The indented central portion 428 may resemble a top surface of a used or partially melted traditional candle, where the wax may have been reduced by melting from the heat of the open flame in order to continue feeding the flame. In other embodiments, the central portion may not be indented. The sidewall 426 and interior wall 427 may cooperate to create a lip 421 on the top surface 422. As seen in the embodiment of FIG. 4A, the sidewall 426 and lip 421 may cooperate to have a varied height thereby resembling the visual appearance of a used traditional candle where the wax has melted due to the flame of the candle. In other embodiments, the sidewall 426 and lip 421 may have a constant height to resemble a new candle that has not melted, as seen in FIG. 4F. In various embodiments, the lip 421 may additionally or alternatively be moldable, such that a user may change the shape. That is, a user may be able to mold the lip 421 to reflect the look of a traditionally used candle and/or mold the lip 421 to reflect the look of a traditionally new(er) candle. The top surface 422 and bottom surface 424 may be circular and the sidewall 426 may extend circumferentially around the longitudinal axis, resulting in a cylindrical body 420. However, other shapes or configurations are possible and within the scope of the invention including, but not limited to, a cube, a cuboid, a cone, a pyramid, or a sphere. The bottom surface 424 may generally be flat, resulting in a stable condition of the candle when placed on a table, shelf, or other suitable flat surface.

The top surface 422, bottom surface 424, and sidewall 426 may cooperate to form a cavity 448. In some embodiments, as illustrated in FIG. 4A and 4F, a cavity wall 446 may define the cavity 448. In some embodiments, the cavity wall 446 may be comprised of a material that is substantially clear. In other embodiments, the cavity wall 446 may be partially transparent. It should be appreciated that any degree of transparency may be used. A cavity wall 446 that is less than opaque may allow light, from an active light source, to transmit outside the cavity 448, thereby making the body 420 of the flameless candle 400 substantially more translucent. In some embodiments, the cavity wall 446 may have one or more regions of varying transparency. For example, an upper cavity wall 446A may be relatively more translucent allowing more light to transmit out to the body 420. A lower cavity wall 446B may be relatively less transparent or opaque. The body 420 that correlates to the lower cavity wall may thus be less translucent. By using a cavity wall region 446A with a relatively greater transparency, flameless candles of the present disclosure may better mimic a traditional candle where regions of the candle at or just below the current wick height are more translucent due to the fact the light has to transmit through less wax. Additionally, by using a cavity wall region 446B with a relatively lower transparency, the flameless candle 400 may better mimic areas of traditional candles substantially below the current wick height where the wax is generally less translucent due to the light being unable to transmit, or transmit with the same brightness, through increasingly thicker areas.

The cavity 448 may house one or more of the internal components. In various embodiments, the internal components may be organized to provide a substantially open area 444. The substantially open area 444 may allow more uninterrupted space for a light source 456 to shine light onto the wax body 420 of the candle. That is, the substantially open area 444 may allow light from a light source 456 to shine from within the cavity onto the body 420 in a generally uninterrupted and, in some cases uniform, manner, which may produce additional luminescence on the body 420. The bottom surface 424 may include a cover 434, that may allow easy access to the power source compartment 436.

The Control Switch

As illustrated in FIGS. 4A and 4F, disposed in the center of the base of the central portion 428 of top surface 422 may be a control switch 430. In various embodiments, the control switch 430 may be a push button, toggle, slide, rotary selector switch, or any other suitable control. In various embodiments, the control switch 430 may be the singular method to control any and all functions or modes of the candle, discussed in more detail below. By activating the control switch 430, one or more functions or modes may be activated, such as the light source 456 may begin to flicker. In alternative or additional embodiments, the bottom surface 424 may include a lower control switch. It is understood that one or more control switches and one or more other methods of activation may be used, separately or in combination, to control the various functions of the flameless candle 400.

In various embodiments, the control switch 430 may include a wick component 431, a light source 456, and a sheath 432. The control switch 430 may generally be configured to resemble a natural candle's wick 431. The wick 431 may be a generally flat or cylindrical structure that protrudes from the indented central portion 428. The wick 431 may resemble a cored wick, a flat braided wick, a square braid wick, or any other wick type. That is, the wick 431 may or may not be braided in appearance. The wick 431 may also have a ball or nub at the tip to resemble the mushrooming or carbonized ball that sometimes develops on natural wicks. In addition, the wick 431 may be relatively thin. In various embodiments, the wick 431 may have a diameter of less than three millimeters. In another embodiment, the wick 431 may be less than one millimeter in diameter. In still other embodiments, the wick 431 may have a diameter of any suitable thickness. The wick 431 may also be relatively short. In various embodiments, the wick 431 may be less than an inch long. In some embodiments, the wick 431 may be less than half an inch long. In a typical embodiment of the present disclosure the wick 431 may be around a quarter inch in length, or shorter. In some embodiments, the wick 431 may be at least partially curved or bent. In other embodiments, the wick 431 may be substantially straight. In some embodiments, the wick 431 may be black to resemble the look of a candle that has been lit at least one time. In other embodiments, the wick 431 may be white. In still another embodiment, the wick 431 may match the color of the body 420. It may be appreciated that the wick 431 may be any color.

In various embodiments, the wick 431 and one or more light sources 456 may be merged to form the control switch 430. That is, the wick 431 and the light source 456 may comprise a single component (the control switch 430) that, for example, may be pushed down to activate or deactivate one or more functions of the flameless candle 400. The wick 431 and light source 456 may be manufactured as a single unit and/or mechanically connected. For example, the light source 456 may be placed into a mold or die, which may be configured to resemble a wick. One or more materials may be injected into the mold such that a control switch 430 resembling a wick 431 is formed on or around the light source 456. In another embodiment, the wick 431 may be glued or fastened to the light source 456 after being molded. In various embodiments, the wick 431 of the control switch 430 may be comprised of plastic or a polymeric material. In other embodiments, the wick 431 may be comprised of glass, rubber, a metal alloy, or any other suitable material or combination of materials.

In some embodiments, as seen in FIGS. 4D and 4E, the control switch 430 may include a sheath 432, which may be formed around the wick 431 and light source 456. In at least one embodiment, the sheath 432 may be formed around the wick 431 and light source 456 before the wick 431 completely dries from the injection molding process. In various embodiments, the sheath 432 may be clear. In other embodiments, the sheath 432 may be semitransparent. In still other embodiments, the sheath 432 may have one or more areas that are substantially opaque. However, it should be appreciated that the sheath 432 may be transparent enough to allow the light from the light source 456 to be transmitted. The sheath 432 may be a plastic, in some embodiments. It should be appreciated that one or more materials may be used individually or in combination to construct the sheath 432.

The Electrical Assembly

The cavity 448 may contain the electrical assembly 450, schematically illustrated in FIG. 4A. The electrical assembly may comprise one or more components, including, but not limited to, a control switch assembly 458, a power source 452, at least one circuit board 454, and a light source 456.

Control Switch Assembly

As seen in FIG. 4C, the control switch assembly 458 may be comprised of one or more components. The control switch assembly 458 components may include, but are not limited to, a control switch 430 (or control switch 430), an internal push button 470, a retaining assembly shell 460, and one or more printed circuit boards (PCBs) 462, 464.

The control switch assembly 458 may comprise a retaining assembly 460. The retaining assembly 460 may have a circumferential portion 468 that mates with a circular opening on an exterior surface 428 (also referred to herein as the indented central portion) of the candle body. In various embodiments, when installed within the body 420, the retaining assembly 460 may be configured to be flush with the surrounding exterior surface 428. In some embodiments, the retaining assembly 460 may have a central lumen 469 through which the control switch 430 may be able to slide. The control switch 430 may be centrally disposed within the central lumen 469. The control switch 430 may be configured such that the light source 456 is flush with the exterior surface 428. For example, the light source 456 may be positioned both partially above and partially below the exterior surface 428. By positioning the light source 456 partially above an exterior surface 428 of the flameless candle 400, the light source 456 may better emulate the bright light of a flame from a traditional candle. By positioning the light source 456 partially below the exterior surface 428, or within the cavity 448, the light may shine from the cavity 448 out onto the sidewall 426 of the body 420 thereby giving a translucent appearance to the body 420. It may be appreciated that the light source 456 may be positioned at any point above or below an exterior surface 428 of the flameless candle 400. Furthermore, it may be appreciated that one or more light sources 456 may be used, such that one or more light sources 456 are located above, or partially above, the exterior surface 428 and one or more light sources 456 are located below, or partially below, the exterior surface 428.

Embodiments of the present disclosure may include one or more printed circuit boards, or PCBs. In one embodiment, the PCBs may include, but are not limited to, a main PCB 454, a light switch PCB 462, and a push button PCB 464. In various embodiments, the light switch PCB 462 and the push button PCB 464 may be located in the control switch assembly 458 and contain electronics for connecting the various components of the control switch assembly together and/or with the main circuit PCB 454. In other embodiments, all or any PCBs may be located exterior to the control switch assembly 458. Any suitable location for any PCBs may be used.

Referring to the embodiment seen in FIGS. 4D and 4E, the control switch 430 may be mechanically and electrically connected to a light switch PCB 462. The light switch PCB 462 may be in direct or indirect electrical communication with the main PCB 454. The control switch 430 may be configured such that it causes the light switch PCB 462 to press, activate, and/or deactivate an internal push button 470. However, in other embodiments, the control switch 430 may directly press upon, activate, and/or deactivate the internal push button 470. The internal push button 470 may be mechanically and electrically connected to a push button PCB 464. The push button PCB 464 may be in direct or indirect electrical communication with the main PCB 454. For example, when a user pushes down onto the control switch 430, the light switch PCB may depress a button 472 on the internal push button 470. The depression of the button 472 may be configured to produce a communication between the internal push button 470 and the push button PCB 464, such as, but not limited to, completing the circuit connecting the push button PCB 464 with the main PCB 454. The main PCB 454 may be configured to cause a signal to run to the light switch PCB 462, thereby activating one or more functions of the light source 456.

The light switch PCB 462 and push button PCB 464 may be optimally arranged, shaped and sized to facilitate light from the light source 456 in the cavity 448 to shine into the open area 444. That is the PCBs 462 and 464 may be relatively small, and positioned in such a way as to facilitate light from the light source 456 positioned on one side of PCBs 462, 464 to shine through or to the other side of the PCBs 462, 464. In one embodiment, the light switch PCB 462 may be configured to be parallel to the light source 456, thereby allowing light to shine from the light source in a substantially 360 degree range, in reference to the light switch PCB 462. The push button PCB 464 may be shaped and sized small enough to allow light to pass on one or more sides into the open area 444 but remain large enough to support the internal push button 470 and any mounting components. In other embodiments, the push button PCB may be shaped and sized to fit substantially within or under the internal push button 470. Any suitable size, shape, and arrangement of the PCBs 462, 464 may be used. In some embodiments, the PCBs 462, 464 may be clear or semi-transparent, thereby increasing the ability of light from the light source 456 to shine from one side of a PCB 462, 464 to the other side and into the open area 444.

Referring back to FIG. 4C, the retaining assembly 460 may comprise one or more components that are assembled to hold the control switch assembly 458 within the candle body 420. The components may, in some embodiments, comprise a mating ring that rests upon the cavity wall 446. The body 420 may secure the retaining assembly 460 into place, on top of the cavity wall 446. In other embodiments, the retaining assembly may be mechanically connected to the cavity wall 446 and/or body 420, for example, using a bayonet connection, a snap fit, a magnetic fit, a friction fit, or any other suitable method of connection. In some embodiments, the configuration of the retaining assembly 460 and the selected material may have desirable translucent, luminescent and aesthetic properties to mimic the look and feel of a traditional candle. In various embodiments, the retaining assembly 460 may be clear. In other embodiments, the retaining assembly 460 may be semitransparent. It may be appreciated that any degree of transparency may be used. It may also be appreciated that the circumferential portion 468 that mates with a circular opening within the top surface 422 may appear opaque and wax like while the rest of the retaining assembly has a higher translucence. A retaining assembly 460 that is less than opaque may allow light from an active light source 456 to better transmit down into the cavity 448, which may in-turn make the body 420 of the flameless candle 400 appear substantially more translucent. In some embodiments, the retaining assembly may be made from a wax, paraffin, glass, polymeric materials, or combinations thereof.

Power Source

Referring again to FIG. 4A, a power source 452 may provide power to the electrical assembly 450, resulting in the light source 456 being illuminated. The power source 452 may be disposed within a power source compartment 436. The power source 452 may comprise one or more batteries 480. The batteries 480 may comprise one or more batteries having one or more sizes or shapes. The power source 452 may be adjacent to the cover 434 and centrally located, allowing an ease of access to change the battery. In other embodiments, the power compartment may be located proximal to the sidewall 426, superior to the rest of the electrical assembly, or exterior to the flameless candle 400. The power compartment may be located in any suitable location. The power source 452 may be one or more standard alkaline batteries, one or more rechargeable batteries, a USB charged power source, a power cord, a power source charged by induction charging, any other suitable source, or any combination thereof Light Source The light source may illuminate the flameless candle. In various embodiments, the light source may be a LED that comprises one or more diodes. In other embodiments, the light source may be an incandescent lamp. In still another embodiment, the light source may be a gas discharge lamp. It may be appreciated that any suitable light source may be used. In various embodiments, different colored lights may be used to better mimic the color of a flame. For example, in one embodiment, the light source may by a combination of red, yellow, orange, and/or white LEDs. The lights may cooperate to mimic the colors of a natural flame. The light source may preferably be located on a midline of the body 420 of the candle in order to mimic traditional candles, as seen in FIG. 4A. In other embodiments, the light source may be located more proximal to the sidewall. In at least one embodiment, the light source may be located superior to the transverse plane, or in the top half of the candle. However, a light source located at any point within the body of the candle is within the scope of the present disclosure.

Circuit Boards

In various embodiments, the main circuit 54 or main PCB 454 may be located anterior to the open area 444 and/or proximal to the power source. In other embodiments, the main circuit 54 or main PCB 454 may be located in any location. The main circuit 54 or main PCB 454 may be the only circuit in some embodiments. In other embodiments, the main circuit 54 or main PCB 454 may be comprised of a plurality of different circuit components. In some embodiments, the circuit board components may include but not limited to, a clock 76, an analog-to-digital converter 80, a random address generator 84, a random sequence generator 90, and an output 92 may be located on the main circuit 54 or main PCB 454. In other embodiments, one or more components may additionally or alternatively be located on the light switch PCB 462, on the push button PCB 464, or on any other circuit. The functionality of the circuit boards 54, 454, 462, and 464 are discussed below.

Function

The following discussion is directed to various functions of the flameless candles 10, 100, 400. While one or more of the various features may be implemented in any number of the disclosed embodiments or any other embodiment contemplated by this disclosure they are described in the context of the following example implementation.

The upper control switch 30, 430 and/or lower control switch 32, herein collectively related to as the control switch, may be in communication with a light source (or light) 56, 456, collectively referred to herein as the light source or light. The control switch may be a push button, toggle switch, slide switch, or any other suitable component. The control switch may be configured to, when selected by the user, modify the frequency of a light's flicker, the luminescence of the light, the color of the light, or the timer settings of the light. In at least one embodiment, the control switch may be a push button, which when depressed selects a particular mode of the candle. In one embodiment, the modes include, but are not limited to, a flicker mode, a static light mode, and an on/off mode. For example, depressing the push button of the control switch may activate the light source in flicker mode. A light in flicker mode may randomly dim and brighten in such a way that mimics a flame from a traditional candle. Depressing the push button a second time may activate the light source in static mode. A light in static mode may be on but may not flicker. Depressing the push button a third time may activate a timer mode. A light in timer mode may automatically turn off after a set time period. Depressing the push button a fourth time may deactivate the light, or result in an off mode. Any suitable means of activation or deactivation of any mode may be used.

In some embodiments, the candle may produce an indication of the mode selected. It at least one embodiment, when the user depresses the control switch, the light source may flash any number of times to indicate a certain mode has been selected.

Flicker Mode

Figure 5A:
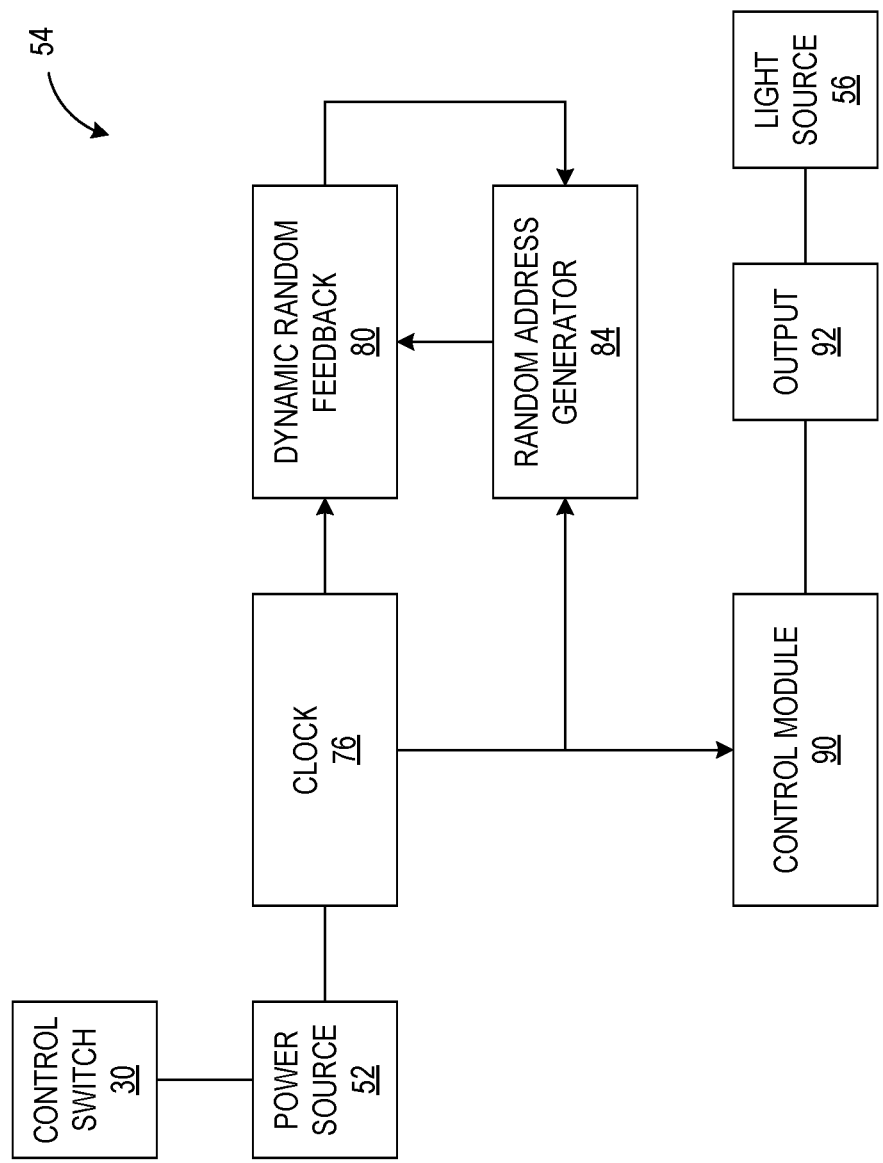
FIG. 5A is a schematic of a circuit board, according to an embodiment of the present disclosure.

The natural flicker may be controlled by one or more methods, including, but not limited to a random signal method. A random signal method may generate one or more random signals resulting in a natural "flicker" from the light source. As noted above, FIG. 5A is an electrical schematic for one embodiment of the circuit board 54 (or PCB 454, and/or in combination with PCB 462 and/or 464) of the present disclosure. Clock 76 may be in electrical communication with the power source 52. When the power source 52, 452 is activated by control switch 30, 32, 432, the clock 76 may provide an input signal to at least the random address generator 84. The random address generator 84 may provide a random signal to the dynamic random feedback 80. The dynamic random feedback 80 may be or may comprise an analog-to-digital converter, in some embodiments. The random signal may vary in one or more aspects including, but not limited to, amplitude, frequency, and duty cycle. The duty cycle may be the period of time it takes for a signal to complete an on-and-off cycle. In at least one embodiment, the random address generator 84 may use pulse-width modulation to modify the signal, which results in controlling the power supplied to the light source. Pulse-width modulation may be used to manipulate (increase or decrease) the power a light source receives at very high rates. This manipulation may result in a perceived flicker as the light source is quickly changed from high luminescence to low luminesce and back again.

The dynamic random feedback 80 may convert the random signal to a digital signal which is then transmitted to the control module 90. The control module may be or may comprise a random sequence generator, in some embodiments. The control module may control one or more light source aspects, including but not limited to light brightness and time. The control module 90 may manipulate the random signal received from the dynamic random feedback 80 into a second random signal; although such is not required. The second random signal may also vary in one or more aspects to control the brightness and duration in the light source. In one embodiment, the second random signal variations may include, but are not limited to, amplitude, frequency, and duty cycle. In at least one embodiment, the control module 90 may also use pulse-width modulation to modify the signal. The second random signal from the control module 90 may be output via output 92 to the light source 56, 456.

Figure 5B:
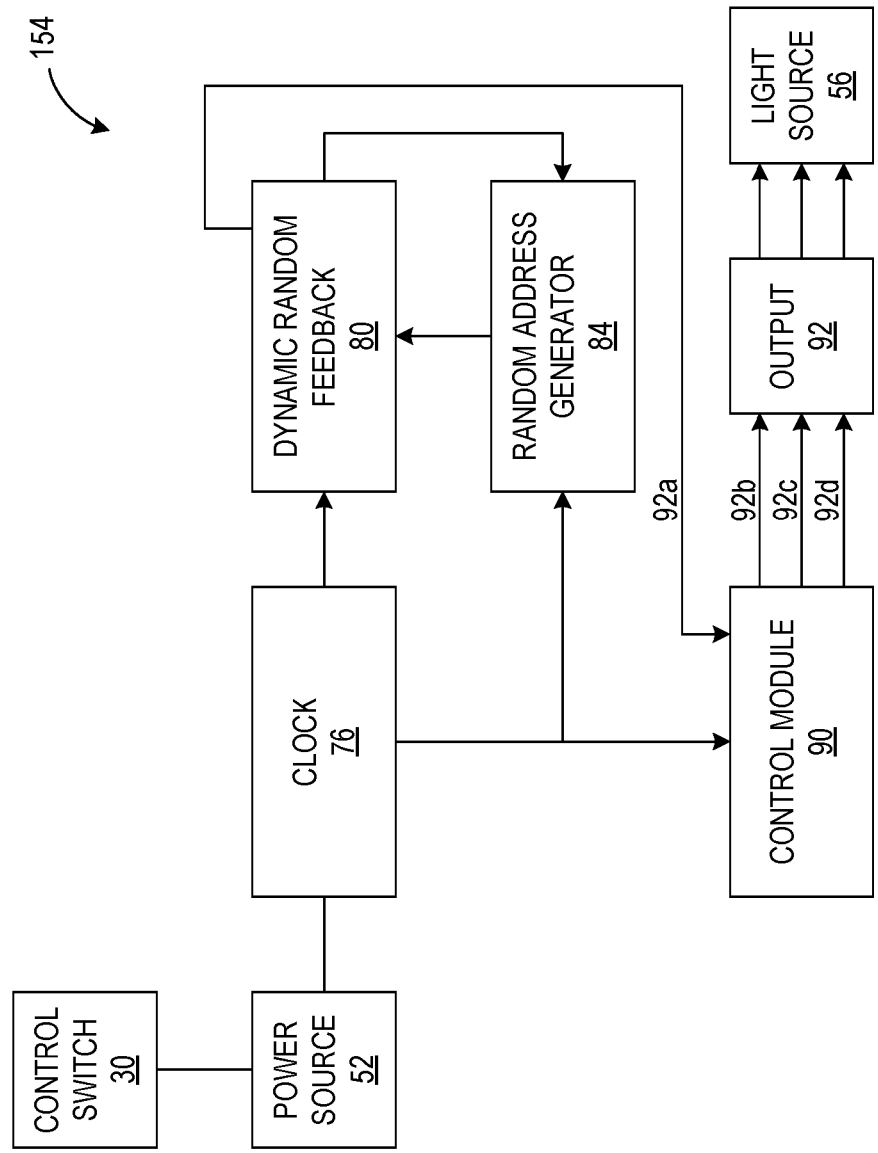
FIG. 5B is a schematic of a circuit board, according to an embodiment of the present disclosure.

In one embodiment, using LED light diodes, the second random signal may be output to one or more diodes. As illustrated in FIG. 5B the control module 90 may convert the random signal 92*a* into one or more random signals 92*b*, 92*c*, and 92*d* each being output to a separate diode via output 92. The signal transmitted randomly to one or more of the diodes of the LED 56, 456 may produce a natural "flicker" of light to the human eye.

The natural "flicker" may have a 72-hour cycle, in some embodiments. A 72-hour cycle may provide an optimal battery life, in some embodiments, where a battery is used as the power source. For example, a random, or seemingly random pattern may be used for a 72-hour cycle, at the end of which the random pattern may then repeat. In some embodiments, a 24-hour cycle may be used. In other embodiments, a 48-hour cycle may be used. It should be understood that a cycle of any duration may be used.

Static Mode

A light source in static mode may be on, and may not flicker. In various embodiments, the static mode may be set to varying degrees of luminosity. That is, the light source may be dimmed to one or more levels. The power supply 52, 452, may supply power directly to the light source 56, 456, in some embodiments. In other embodiments, the power supply may pass through the clock 76 before reaching the light source 56, 456, thereby allowing a timer mode to be activated.

Timer Mode

The flameless candle may have a timer, where the light remains on for a predetermined timed period. In some embodiments, the timed period may be automatically set. For example, activation of the timer may keep the light source on for one hour and then turn the candle off. In other embodiments, the user may set the timer to any desired time. In one embodiment, the user may select the timer by depressing a control button until the timer mode is selected. In one example, the light source may flash three times to indicate the timer mode has been selected. The user may then push the control switch any number of desired times, each depression of the control switch adding a predetermined period of time. In other embodiments, there may be a USB port that a user may plug into the candle with preloaded timer settings. In still another, there may be a separate control switch for the timer mode, or two or more control switches may, together, activate the timer mode. Any suitable method to set a timer for the candle may be used.

Scented Flameless Candle

A flameless candle of the present disclosure may additionally or alternatively have a scented component that may provide a scent or aroma to the surrounding environment. In some embodiments, the scented component may be a scented cartridge. The scent may be diffused through the cartridge and into the surrounding environment when heat or an electric current is applied to the scent cartridge, in some embodiments.

Figure 6:
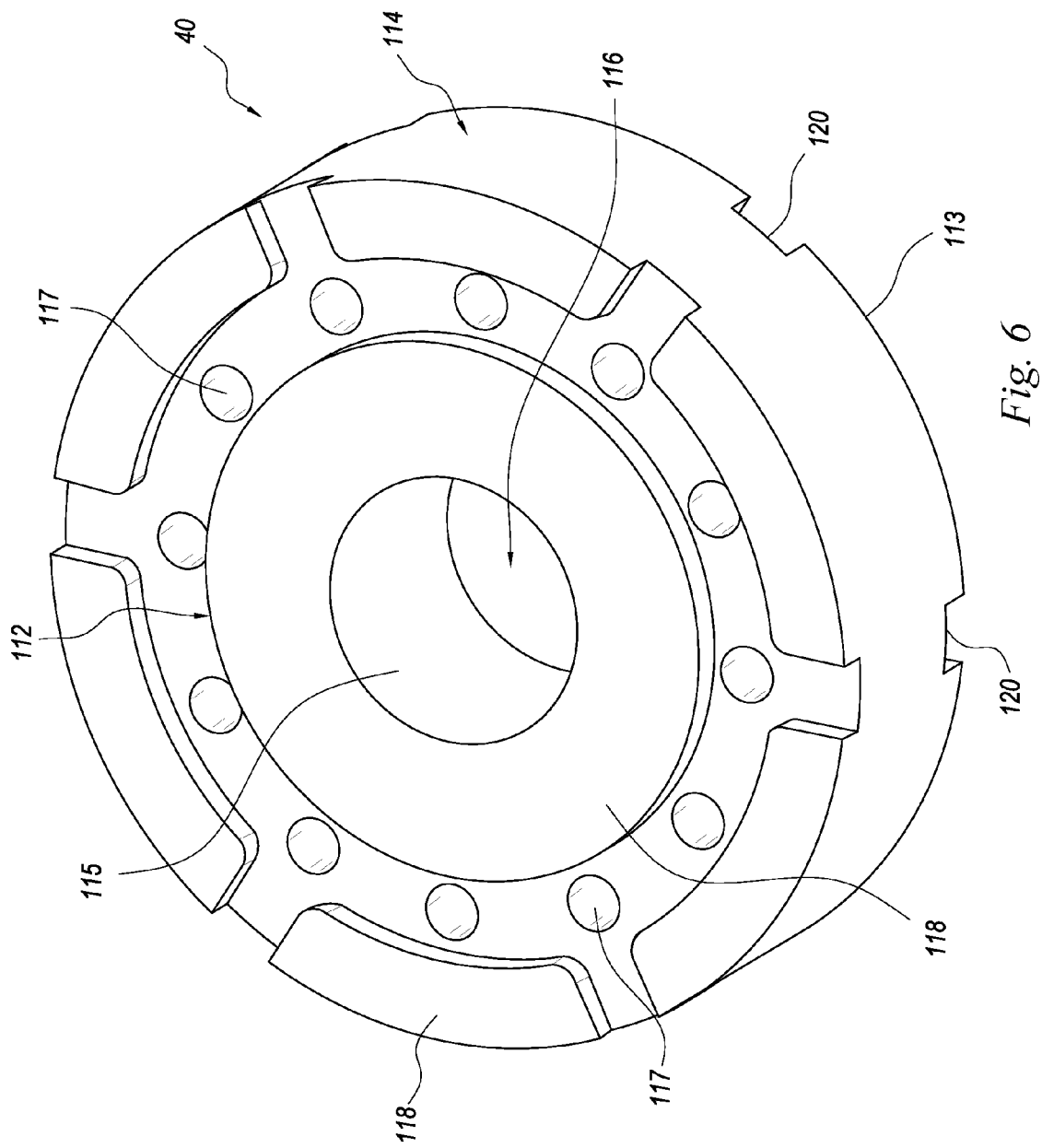
FIG. 6 is a perspective view of a scent cartridge, according to an embodiment of the present disclosure.

Referring to FIG. 6, a scent cartridge 40, may be comprised of a top surface 112, a bottom surface 113, and an outer sidewall 114 that extends between the bottom surface 113 and the top surface 112. In some embodiments, the scent cartridge 40 may further comprise an inner sidewall 115, extending between the bottom surface 113 and the top surface 112, thereby defining a hole 116. The top surface 112, bottom surface 113, and sidewalls 114, 115 may cooperate to define a chamber, or cavity 119 (seen in FIG. 7). The cavity 119 may contain one or more fragrance impregnated materials. In one embodiment, the fragrance impregnated material may be a fragrant liquid. In another embodiment, the fragrance impregnated material may be a fragrant disk. Any suitable fragrant material may be used.

The top surface may comprise one or more openings 117 through which a fragrance vapor, or scent, may be diffused. The openings 117 may have a diameter that is between five and ten percent of the outer diameter of the scent cartridge 40, in various embodiments. In some embodiments, the openings 117 have a diameter between about two millimeters and twenty millimeters. In other embodiments, the openings may have any suitable diameter. It should also be understood the openings 117 may be circular holes, slats, or any other suitable opening for diffusing the scent. The openings 117 may have a depth that is less than the height of the outer sidewall 114, in some embodiments. In other embodiments, the openings may have a depth equal to the height of the outer sidewall 114. In still other embodiments, there may be openings 117 on the surface of inner sidewall 115 or outer sidewall 114. The top surface 112 may comprise a plurality of surface features 118. Surface features 118 may include, but are not limited to, bumps, ridges, protrusions, channels, and reliefs. Surface features 118 may further assist with diffusing the scent.

The bottom surface 113 of the scent cartridge 40 may be flat, in some embodiments. In other embodiments, the bottom surface 113 may have surface features 120 that allow the bottom surface to rest properly without shifting within the flameless candle 10, 400. In at least one embodiment, the bottom surface 113 has a plurality of surface features 120 that engage with surface features on the indented central portion 28 of the flameless candle 10, 400. By rotating the scent cartridge 40, the surface features on the bottom surface 113 may substantially align and/or lock with the surface features on the flameless candle 10, 400 to hold the scented cartridge 110 in place. In some embodiments, the top surface 112 may have the same configuration of surface features 120 as the bottom surface 113 allowing the scent cartridge 40 to be flipped or turned over for prolonged use.

The light source, as discussed above, may be disposed inside the body of the candle, within the control switch assembly, or in any other suitable position. In at least one embodiment, the light source may be disposed within a central portion of the scent cartridge, allowing the user to replace the light and the scent simultaneously.

Figure 7:
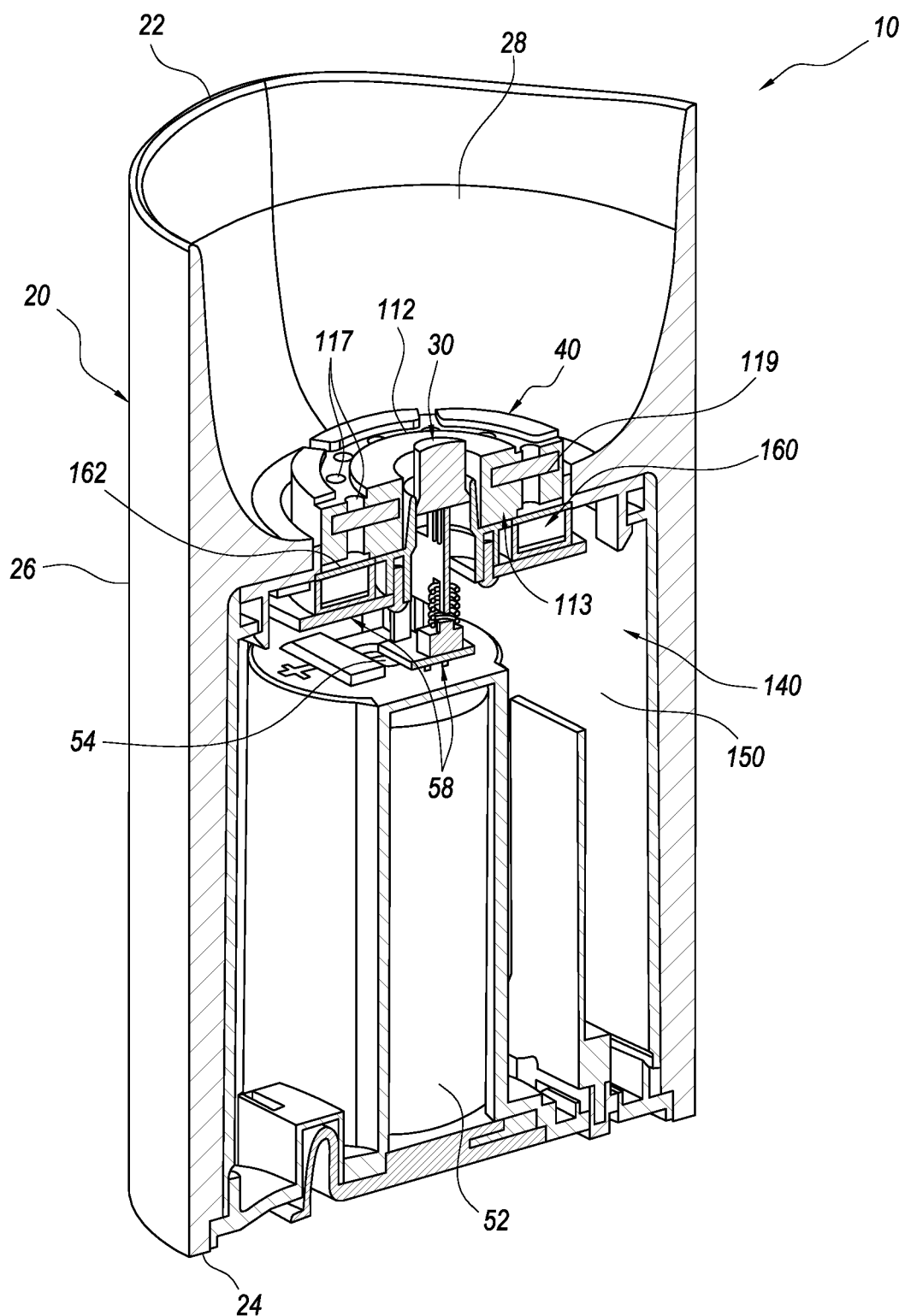
FIG. 7 is a cross-section of a flameless pillar candle, according to an embodiment of the present disclosure.

Referring to FIG. 7, a scent cartridge 40 may be disposed within the indented central portion 28, 428 of flameless candle 10, 400. In at least one embodiment, the bottom surface 113 of the scent cartridge 40 may be flush with the base of the indented central portion 28, 428. In other embodiments, as seen in FIG. 7, the hole 116 may be positioned over a control switch 30, 430, the control switch 30, 430 at least partially extending outwardly from the scented cartridge 40. In still other embodiments, the scented cartridge may be positioned to act on the control switch. For example, the scented cartridge which may, for example, have no hole 116, may be placed in the indented central portion 28, 428. A user may be able to push onto the scented cartridge, which may in-turn push onto a push button control switch, thereby depressing the control switch. In still other embodiments, a control switch 30, 430 may be integrated into the scent cartridge.

Activation of a control switch may 30, 430, in addition to activating a light source 56, 456, turn on or off a heating element 160 or otherwise activate the scent mode of the candle. To provide heat to the scent cartridge 40, the flameless candle 10, 400 may further comprise a heating element 160, which may be in direct contact with, in nearly direct contact with, adjacent to, or otherwise close to the scent cartridge 40. However, any suitable position allowing the heating element 160 to heat the scent cartridge 40 may be used. The heating element 160 may also be in communication with the circuit board 54, 454. In at least one embodiment, the heating element 160 may be situated between the control switch assembly 58, 458 and the scent cartridge 40. In one embodiment, the heating element 160 may have an outer surface 162 that cooperates, or mates, with the bottom surface 113 of the scent cartridge 40, in order to apply direct heat. When a user selects to activate the heating element 160, heat may be applied to the bottom surface 113 of the scent cartridge 40, resulting in an emission or diffusion, of the fragrant scent.

Figure 8:
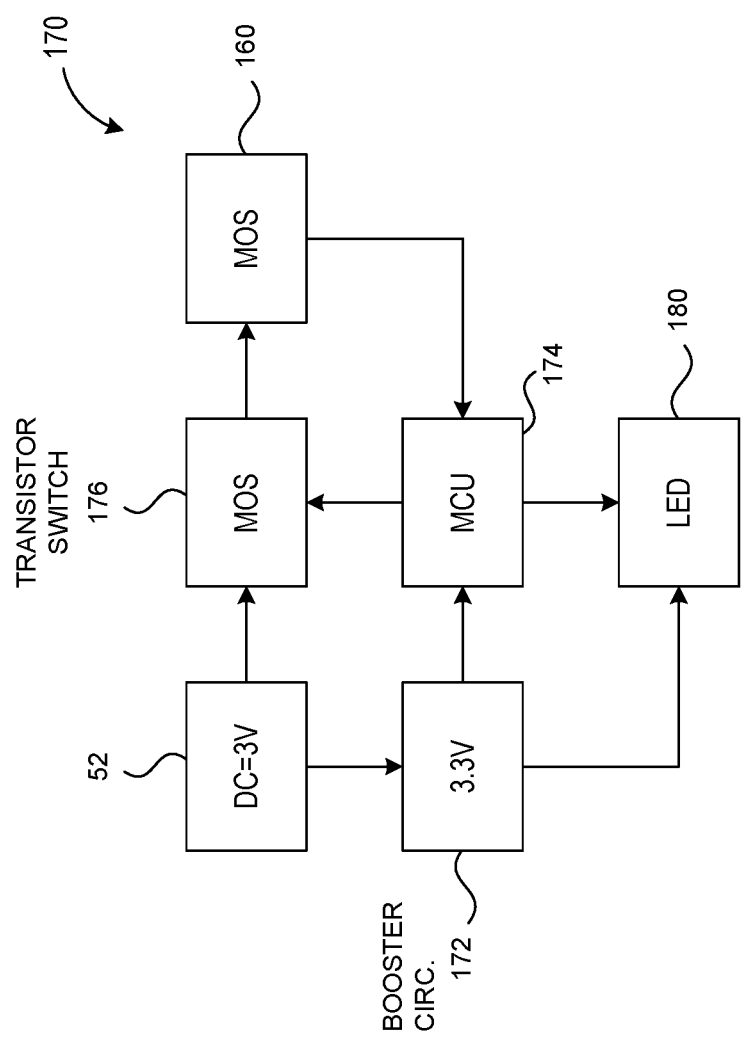
FIG. 8 is a schematic of a circuit board with a heating element, according to an embodiment of the present disclosure.

FIG. 8 illustrates an example circuit schematic for the circuit board in an embodiment involving a heating element. The circuit 170 may comprise a power source 52, 452, a booster circuit 172, an MCU detection circuit 174, a transistor switch 176, and the heating element 160. In some embodiments, the circuit may also include a light source circuit 180. The light source circuit may, in some embodiments, be a circuit such as that illustrated by FIG. 5A, discussed above. The light source circuit and heating element circuit may share some or all common components. The power source 52, 452 may provide a voltage to the MCU detection circuit 174 through the booster circuit 172, in some embodiments. In other embodiments, the power source 52 may provide a voltage directly to the MCU detection circuit. The booster circuit 172 may amplify the voltage obtained from the power source 52, 452 and provide it to the MCU detection circuit 174. In various embodiments, the booster circuit 172 may provide an amplified voltage to the light source circuit 180. The MCU detection circuit 174 may output high and low electric levels to control the transistor switch 176. The transistor switch 176 may connect the MCU detection circuit 174 with the heating element 160, thereby affecting one or more heating element modes as well as the temperature of the heating element 160. Heating element modes may include, but are not limited to, on, on-high, on-low, off, or timer.

In various embodiments, based on one or more control switch 30, 32, 432 inputs, the MCU detection circuit 174 may output various high and low electric levels over a desired time period, herein referred to as high-low cycle. The high-low cycle may enable a cyclic on and off interval of heating by turning the transistor switch 176 on and off based on the electric levels. For example, a user may select a scent feature mode having a duration of four hours. The MCU detection circuit 174 may output a high-low cycle resulting in the transistor switch 176 turning the heating element 160 on for thirty minutes, off for two hours, on for ten minutes, off for thirty minutes, on for ten minutes, off for thirty minutes, and then off In such an embodiment, when the control switch 30, 32, 430 is pressed again, the cycle may be cancelled and the light source 56, 456 may turn off.

The MCU detection circuit 174 may incorporate a temperature sensor 182, as shown in the detailed circuit schematic example of FIG. 9. By converting the temperature change of the heating plate to a voltage change, the temperature of the heating plate can be tested and controlled by the MCU detection circuit 174. When the temperature is equal to or greater than a desired value, the MCU detection circuit 174 may turn the transistor switch 176 off, resulting in cutting off power to the heating element 160. The desired high temperature value may be, at least in part, dependent upon at least the material properties of the scent cartridge 40. In at least one embodiment, the desired high temperature value may be about fifty degrees Celsius (one-hundred and twenty two degrees Fahrenheit). In general, the desired high temperature value can be between about forty-five degrees Celsius (about one-hundred and thirteen degrees Fahrenheit) and fifty-five degrees Celsius (about one-hundred and thirty one degrees Fahrenheit). When the temperature is equal to or lower than a desired value, the MCU detection circuit 174 may turn the transistor switch 176 on, sending power to the heating element 160, and thereby turning the heating element 160 on. In at least one embodiment, the desired low temperature value may be about five degrees Celsius lower than the desired high temperature value. The desired low temperature value may be, at least in part, dependent upon the material properties of the scent cartridge 40. In at least one embodiment, the desired low temperature value is about forty-five degrees Celsius (about one-hundred degrees Fahrenheit). In general, the desired low temperature value can be between about thirty-eight degrees Celsius (about one-hundred degrees Fahrenheit) and fifty degrees Celsius (about one-hundred and twenty-two degrees Fahrenheit). However, it should be understood that any suitable temperature (s) to heat the heating element 160 may be used and are within the scope of the present disclosure.

In at least one embodiment as shown in FIGS. 4B and 4G, the sleeves 410A, 410B may incorporate a scent. A user may be able to remove and exchange the sleeve, as discussed above, in order to change the scent. A heating element, fan, or other method to disperse the scent may be located on the inner core 400B. The heating element 160, a fan, and/or any other suitable method may be activated using one or more control switches 30, 430, as discussed above.

Sensing Flameless Candle

A flameless candle of the present disclosure may additionally or alternatively have a sensing component, in various embodiments. In some embodiments, the sensing component may be a motion sensor that may allow a user to use hand motions, or other motions, to select various functions, or modes, of the flameless candle. The modes may include, but are not limited to, whether the light is on or off, whether the light is in a static mode or flicker mode, the duration the light is on, the color of the light, the luminescence of the light, and whether a scent mode is on. In other embodiments, the sensing component may be an optical sensor that may allow one or more modes to be selected based on the ambient light in the surrounding environment. For example, when the ambient light is reduced, such as at dusk, the optical sensor may detect the change and turn the flameless candle's light on. In still other embodiments, the sensing component may be an audio sensor that may allow the user to use audio cues to select various functions, or modes, of the flameless candle. In one embodiment, the sensing component may be able to detect air movement, allowing a user to select a various mode, such as turning the flameless candle off, by blowing on the sensor, simulating a method of blowing out a traditional true flame candle. In some embodiments, the sensing component may be a Bluetooth, radio, or other wireless component able to receive a wireless signal from a computer, remote, handheld device, or any other suitable device. For example, a user may select a flicker mode on a timer for two hours from her handheld device. The device may transmit a signal that may be received by the sensing component in the wireless candle, resulting in the candle being configured to remain in flicker mode for two hours and then turn off. One or more sensors may be used in various embodiments of the present disclosure.

Figure 9A:
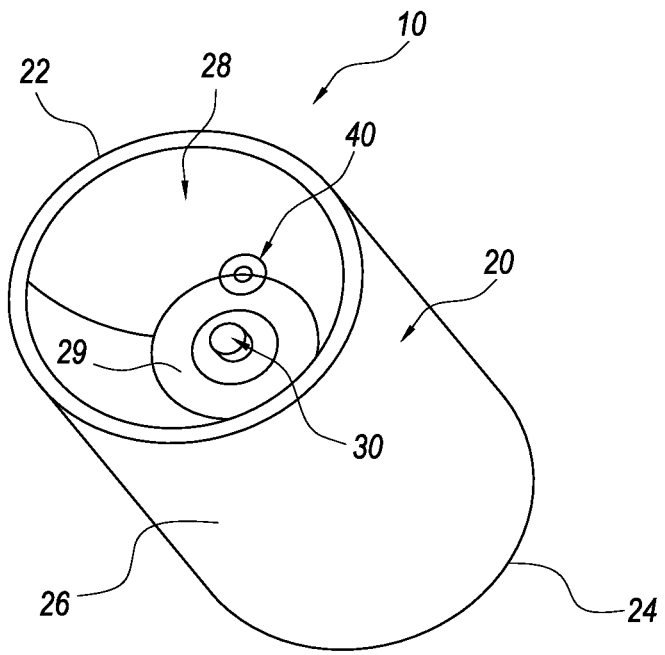
FIG. 9A is a perspective view of a flameless candle with a sensor, according to an embodiment of the present disclosure.
Figure 9B:
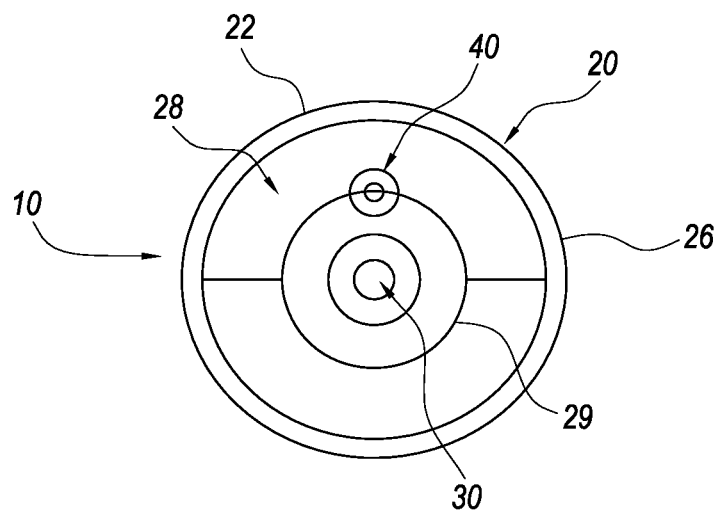
FIG. 9B is a top view of a flameless candle with a sensor, according to an embodiment of the present disclosure.
Figure 10:
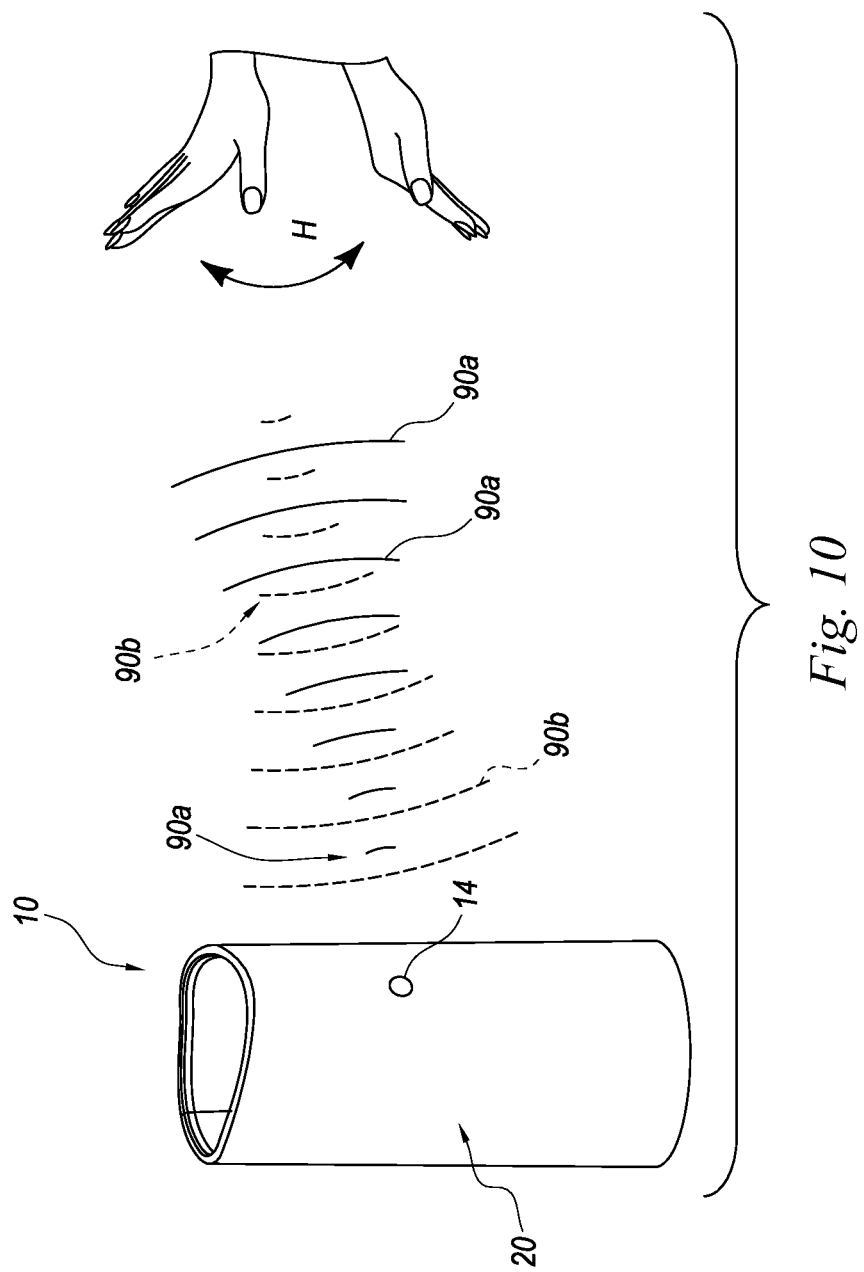
FIG. 10 illustrates how a motion sensor functions with a flameless pillar candle, according to an embodiment of the present disclosure.

A flameless candle may comprise a motion sensor, in various embodiments. As seen in FIGS. 9A-9B a motion sensor 70 may be disposed within the indented central portion 28. In some embodiments, the motion sensor 70 may be radially offset from the center of the base 29 of the central portion 28, 428. In various embodiments where a scent cartridge may be used, the motion sensor 70 may be spaced sufficiently away from the center of the base 29 so as not to be covered by the scent cartridge. In some embodiments, the motion sensor 70 may be integrated with the upper control switch 30, 430. In at least one embodiment the motion sensor 70, upper control switch 30, 430, and light source 56, 456 may be collectively integrated. In other embodiments as seen in FIG. 10, the motion sensor 70 may be embedded within the body 20, 420 of the flameless candle 10, 400. By embedding the motion sensor 70 into the body 20, 420 of the flameless candle 10, 400, the candle may have additional functionality while being aesthetically similar to a traditional candle. Any suitable location to embed the motion sensor 70 may be used and is within the scope of the present disclosure.

Figure 11:
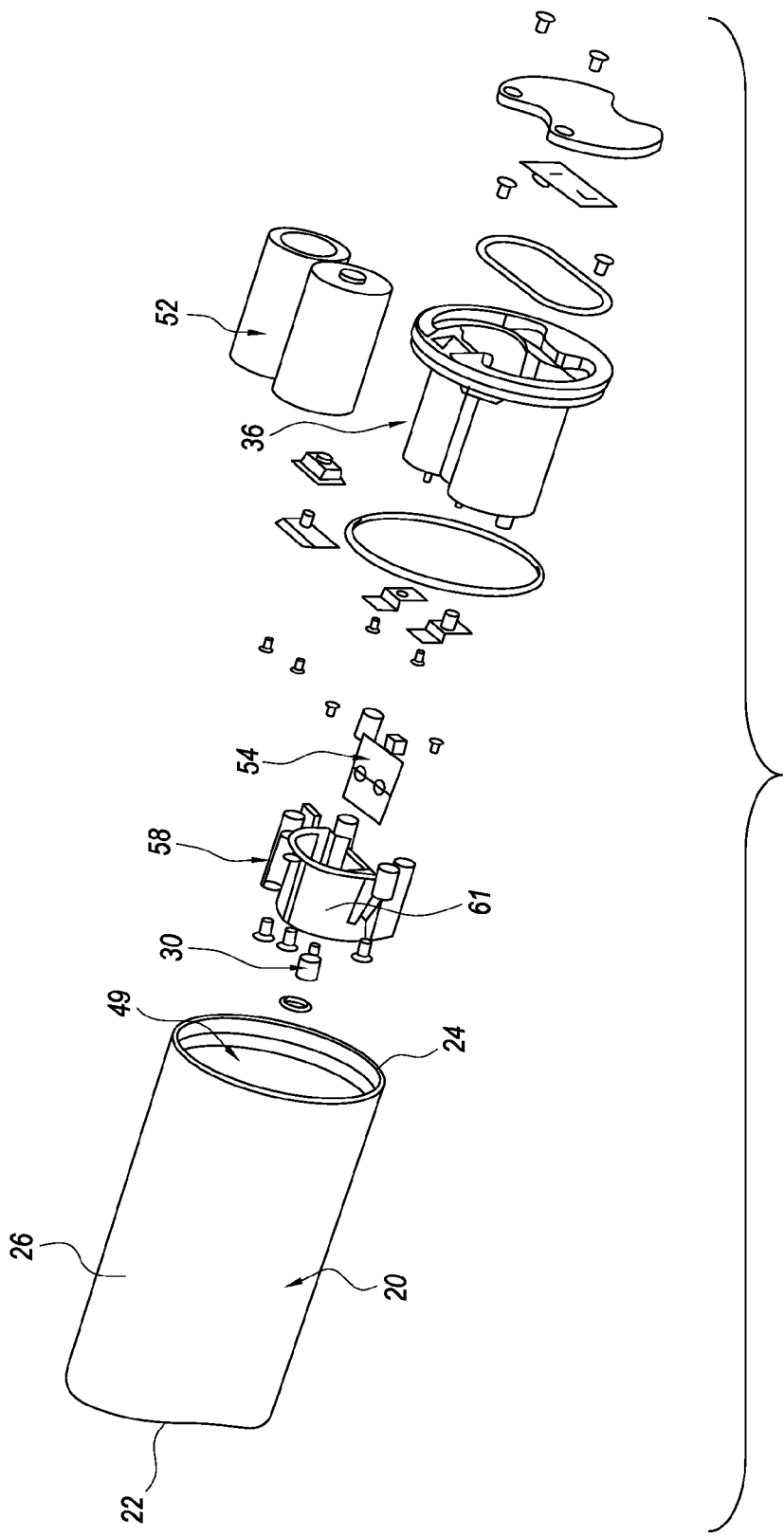
FIG. 11 is an exploded view of a flameless candle, according to an embodiment of the present disclosure.

A motion sensor assembly may house the motion sensor. Similar to the control switch assembly discussed above, the motion sensor assembly may be in communication with the power source, the light source, and a circuit board. Referring additionally to the exploded view in FIG. 11, when installed within the cavity 49, the motion sensor assembly 61 may be flush with the surrounding surface of the body 20, 420 and/or may be flush with the indented central portion on the top surface 22, 422. In some embodiments, the motion sensor assembly 61 is made from a wax, paraffin, glass, polymeric materials, or combinations thereof. In some embodiments, the configuration of the motion sensor assembly and the selected material may have desirable translucent, luminescent and aesthetic properties to mimic the look and feel of a traditional candle.

The motion sensor may emit electromagnetic waves. By using different hand motions, electromagnetic induction modules may produce different waveform outputs to perform different product function statuses (such as on or off). In various embodiments, by activating the motion sensor 70, the light source 56, 456 of the candle may be illuminated. In at least one embodiment, a control switch may activate the power supply before the motion sensor may change the mode.

Figure 12:
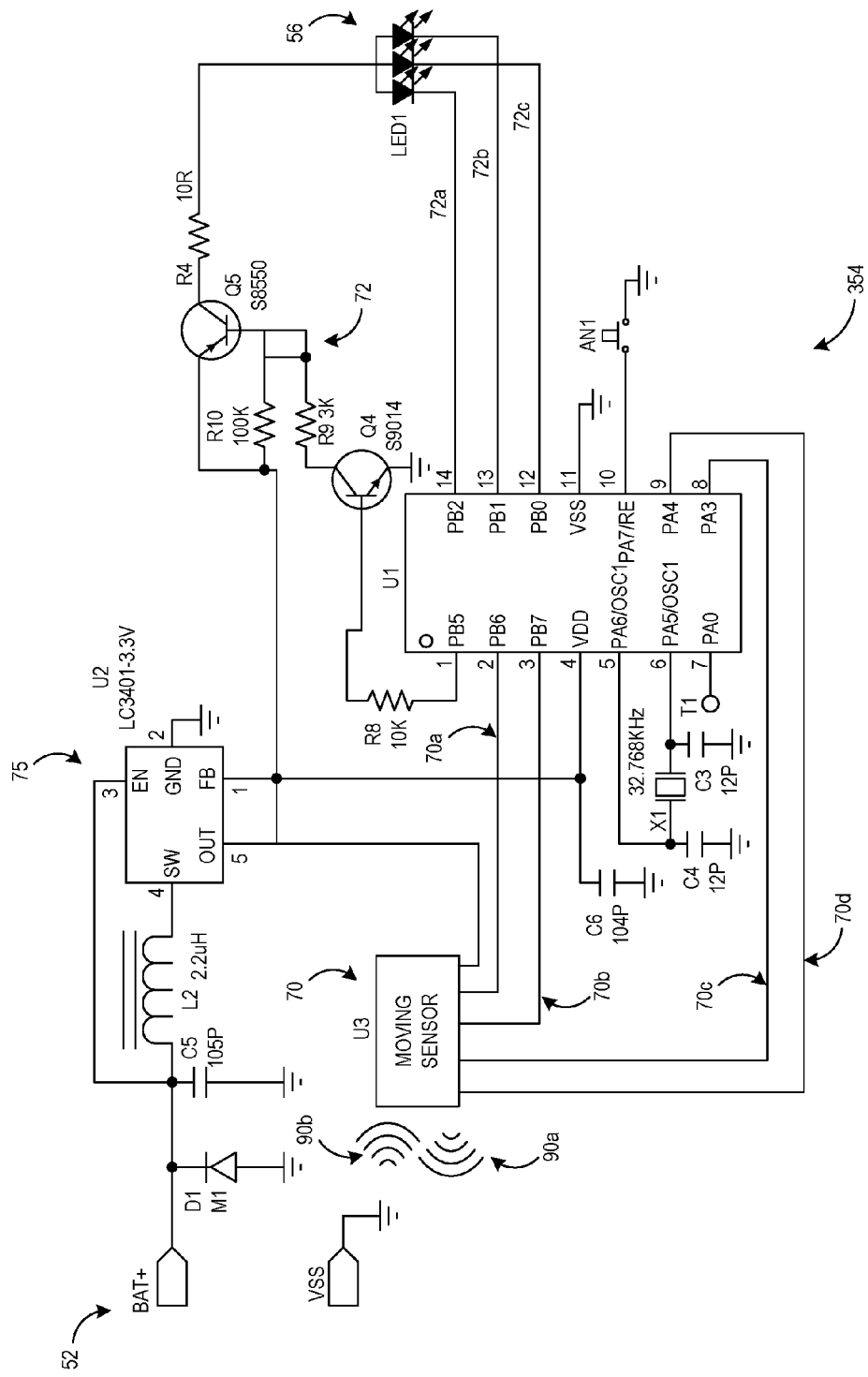
FIG. 12 is a schematic of a circuit board with a motion sensor, according to an embodiment of the present disclosure.

Referring additionally to FIG. 12, which is an electrical schematic for one embodiment involving a motion sensor, as power is supplied from the power source 52 optionally through a booster circuit 75 to the motion sensor 70, the motion sensor 70 may emit electromagnetic waves 90*a*.

Based on different motions at a certain distance, the electromagnetic waves may be reflected and the motion sensor 70 may receive the different electromagnetic waves 90b. Through the internal processing of the motion sensor 70, the motion sensor 70 may output one or more signals 70a, 70b, 70c, and 70d to the control circuit 55, which may be connected to the light source 56. Based on the signal(s) 70a, 70b, 70c, and 70d received from the motion sensor 70, the control circuit 55 may adjust, among other features, the brightness or color of the light, the emission of scent, turn the light source 56, 456 on or off, adjust any other mode or function, or perform any combination thereof.

In one particular embodiment, the light source 56, 456 may be off and the candle may be in a standby mode. When the power source 52, 452 is turned on, at least one oscillator of the control circuit 55 may output a high level voltage continuously to a transistor circuit 72 of the circuit board 354. This high level voltage may be continuously supplied to a first transistor of the transistor circuit 72 until it reaches a saturation conduction. The voltage may then pass through to a second transistor of the transistor circuit 72, whereby the second transistor is conducted. The voltage may then pass to the light source 56, 456, in essence turning the light source on. The voltage may then pass back to the control circuit 55 as three outputs 72A, 72B, and 72C. The three outputs 72A, 72B, and 72C may form square wave outputs, thereby affecting the amplitude of the voltage provided to the light source, which may cause the light source 56 to flash. In some embodiments, the control circuit 55 may utilize pulse modulation to control brightness of the light source 56, 456.

Figure 13:
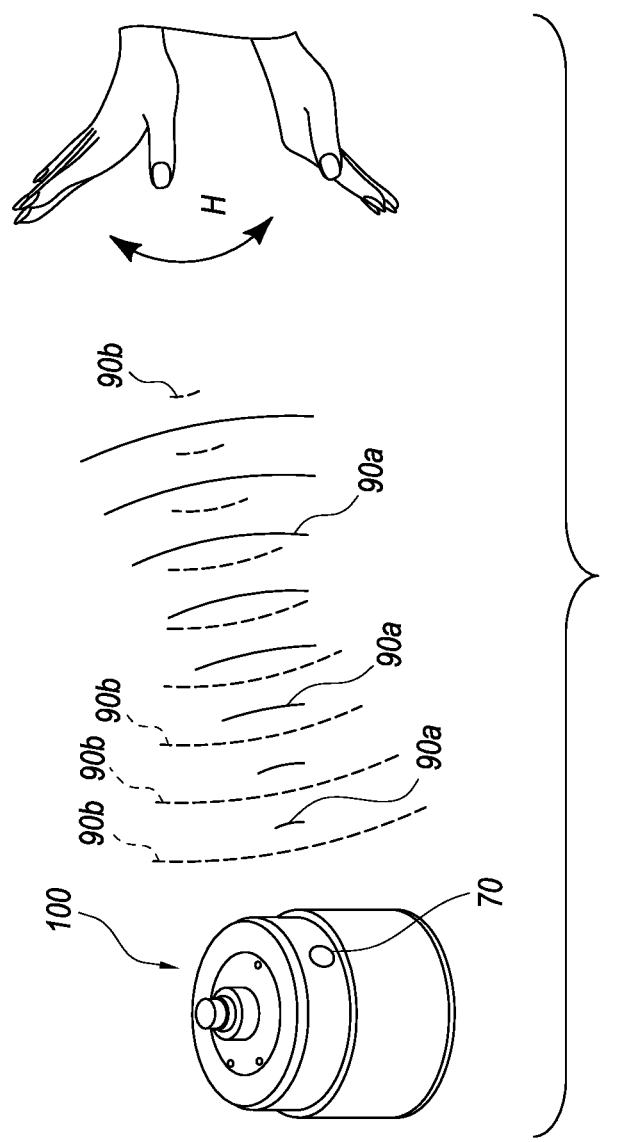
FIG. 13 illustrates how a motion sensor functions with a flameless votive candle, according to an embodiment of the present disclosure.

FIGS. 10 and 13 illustrate different embodiments of a flameless candle with the motion sensor in use. The motion sensor 70 may emit a plurality of electromagnetic waves 90a that proceed unimpeded until a user's hand H makes a gesture, motion, or movement. The movement may reflect the electromagnetic waves 90b back to the motion sensor 70. As discussed above, through the internal processing of the motion sensor 70, the motion sensor converts the reflected electromagnetic waves 90b into output signals that are processed by a control circuit of the candle. The motion sensor 70 may have a working range of about five meters (about seventeen feet). In other embodiments, the motion sensor 70 may have a working range of ten meters (about thirty-three feet). In one embodiment, the motion sensor may have a range of over ten meters. The motion sensor 70 may have any desired working range in various embodiments of the present disclosure.

While various features of various embodiments of the present disclosure are described with respect to particular embodiments for ease of discussion, it is appreciated that any or all of the various features of one embodiment may be additionally used with any of the other embodiments described herein.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

I claim:

1. An electronic candle, comprising:
 a body comprising a top surface, a bottom surface, one or more sidewalls between the top surface and the bottom surface, and a cavity defined by the top surface, the bottom surface and the one or more sidewalls, the top surface including a lip having a varied height resembling a visual appearance of a used traditional candle where candle wax has melted due to a true candle flame, the top surface further including an indented central portion with a circular opening;
 a light source including an LED positioned within the body and accommodated within the indented central portion of the top surface, the light source configured to electrically operate and to illuminate in a way that simulates a natural flicker of a real candle flame; and
 a wick component positioned above the indented central portion, the wick component appearing substantially black in color and being visible to a viewer of the electronic flameless candle, the wick component configured in shape and size to simulate a true flame candle's wick, wherein the wick component is coupled to a spring which allows the wick component to be pressed upon receiving a force on the wick component.

2. The electronic candle of claim 1, wherein the light source is configured to produce light variations that appear as random flicker.

3. The electronic candle of claim 2, wherein the random flicker is produced in response to a random signal that varies in at least one of amplitude, frequency, or duty cycle.

4. The electronic candle of claim 3, wherein the random signal forms part of a pulse-width modulation signal.

5. The electronic candle of claim 3, including:
 a battery compartment positioned within the cavity; and
 an electronic circuit board positioned on a top section of the battery compartment, the electronic circuit board configured to produce the random signal that varies in at least one of amplitude, frequency, or duty cycle.

6. The electronic candle of claim 1, further including a control switch positioned on a bottom side of the electronic candle.

7. The electronic candle of claim 6, wherein the control switch is configured to (a) turn the electronic candle on and off, or (b) enable an operation of a timer associated with the electronic candle, the timer allowing the light source to automatically turn off after a predetermined period of time during which the light source has remained illuminated.

8. The electronic candle of claim 7, wherein the control switch is configured to activate the operation of the timer function upon being depressed.

9. The electronic candle of claim 7, wherein the light source is configured to flash a particular number of times to indicate selection of a particular timer mode of operation.

10. The electronic candle of claim 7, wherein the control switch is configured to set a duration of the timer based on a number of depressions received by the control switch.

11. The electronic candle of claim 6, wherein the control switch is configured to enable the operation of the light source in (a) a steady mode of operation, or (b) in a flicker mode of operation.

12. The electronic candle of claim 1, wherein one or more walls of the cavity are partially transparent.

13. The electronic candle of claim 1, comprising a control switch comprising the light source.

14. The electronic candle of claim 1, wherein at least a portion of light that emanates from the light source passes through a partially transparent material.

15. The electronic candle of claim 14, wherein the partially transparent material forms a sheath that encapsulates the light source.

16. The electronic candle of claim 1, wherein the light source is positioned to transmit light above an exterior surface of the cavity, as well as below the exterior surface into the cavity.

17. The electronic candle of claim 1, wherein the top lip is moldable so as to allow a shape of the top lip to be modified by a user.

18. The electronic candle of claim 1, further including a remote control device operable to communicate remotely with the electronic candle and to control one or more operations of the electronic candle.

19. The electronic candle of claim 18, wherein the one or more operations of the electronic flameless candle includes enabling a timer operation.

* * * * *